US011633113B2

(12) United States Patent
Eberle et al.

(10) Patent No.: US 11,633,113 B2
(45) Date of Patent: Apr. 25, 2023

(54) OPTICAL SENSOR ASSEMBLIES AND METHODS

(71) Applicant: Phyzhon Health Inc., Rancho Cordova, CA (US)

(72) Inventors: Michael J. Eberle, Fair Oaks, CA (US); Diana Margaret Tasker, Sacramento, CA (US); Howard Neil Rourke, Sacramento, CA (US)

(73) Assignee: Phyzhon Health Inc., Folsom, CA (US)

( * ) Notice: Subject to any disclaimer, the term of this patent is extended or adjusted under 35 U.S.C. 154(b) by 344 days.

(21) Appl. No.: 15/765,546

(22) PCT Filed: Oct. 7, 2016

(86) PCT No.: PCT/US2016/056098
§ 371 (c)(1),
(2) Date: Apr. 3, 2018

(87) PCT Pub. No.: WO2017/062839
PCT Pub. Date: Apr. 13, 2017

(65) Prior Publication Data
US 2018/0228385 A1 Aug. 16, 2018

Related U.S. Application Data

(60) Provisional application No. 62/239,624, filed on Oct. 9, 2015.

(51) Int. Cl.
*A61B 5/01* (2006.01)
*A61B 5/0215* (2006.01)
(Continued)

(52) U.S. Cl.
CPC ........ *A61B 5/02154* (2013.01); *A61B 5/6851* (2013.01); *G01L 11/025* (2013.01);
(Continued)

(58) Field of Classification Search
CPC ............ A61B 5/02154; A61B 2562/12; A61B 5/6851; A61B 2562/0271; A61B 5/02158;
(Continued)

(56) References Cited

U.S. PATENT DOCUMENTS 3,932,160 A 1/1976 Camlibel et al.
3,989,350 A 11/1976 Cohen et al.
(Continued)

FOREIGN PATENT DOCUMENTS

EP 1434072 A1 6/2004
WO WO-235268 A1 5/2002
(Continued)

OTHER PUBLICATIONS

Mendez A., "Fiber Bragging Grating Sensors: A Market Overview", Jul. 2, 2007, Third European Workshop on Optical Fibre Sensors, vol. 6619 (Year: 2007).*
(Continued)

*Primary Examiner* — Patricia J Park
*Assistant Examiner* — Adil Partap S Virk
(74) *Attorney, Agent, or Firm* — Schwegman Lundberg & Woessner, P.A.

(57) ABSTRACT

An optical connector including a first optical fiber having a first diameter and having a core that includes a thermally expanded core portion adjacent a first end of the first optical fiber, a second optical fiber spliced to a second end of the first optical fiber, the second optical fiber having a second diameter less than the first diameter, and a connector bore having a first bore portion configured to receive the first end of the first optical fiber.

18 Claims, 11 Drawing Sheets

(51) Int. Cl.
*A61B 5/00* (2006.01)
*G01L 11/02* (2006.01)
*G02B 6/255* (2006.01)
*G02B 6/26* (2006.01)
*G02B 6/38* (2006.01)

(52) U.S. Cl.
CPC ........... *G02B 6/2552* (2013.01); *G02B 6/262* (2013.01); *G02B 6/3846* (2013.01); *A61B 5/01* (2013.01); *A61B 5/02158* (2013.01); *A61B 2562/0247* (2013.01); *A61B 2562/0266* (2013.01); *A61B 2562/0271* (2013.01); *A61B 2562/043* (2013.01); *A61B 2562/063* (2013.01); *A61B 2562/12* (2013.01); *G02B 6/255* (2013.01); *G02B 6/2551* (2013.01)

(58) Field of Classification Search
CPC .............. A61B 5/01; A61B 2562/0247; A61B 2562/0266; A61B 2562/043; A61B 2562/063; G01L 11/025; G02B 6/2552; G02B 6/262; G02B 6/3846; G02B 6/2551; G02B 6/255
See application file for complete search history.

(56) References Cited

U.S. PATENT DOCUMENTS

| | | | |
|---|---|---|---|
| 4,452,508 A | 6/1984 | Beales et al. | |
| 5,085,223 A * | 2/1992 | Lars | G01L 9/0077 73/706 |
| 5,125,058 A * | 6/1992 | Tenerz | A61B 5/02154 128/898 |
| 5,594,825 A | 1/1997 | Kawasaki | |
| 6,112,598 A * | 9/2000 | Tenerz | G01L 19/147 73/756 |
| 7,920,763 B1 | 4/2011 | Shou et al. | |
| 8,559,770 B2 | 10/2013 | Donlagic et al. | |
| 11,026,591 B2 * | 6/2021 | Burkett | A61B 5/6851 |
| 2002/0150332 A1 | 10/2002 | Aldridge et al. | |
| 2002/0154860 A1 * | 10/2002 | Fernald | G01L 11/025 385/37 |
| 2004/0175073 A1 | 9/2004 | Grinderslev et al. | |
| 2011/0190640 A1 * | 8/2011 | Bremer | C03C 25/68 600/478 |
| 2013/0022308 A1 * | 1/2013 | Wild | A61B 5/0215 385/12 |
| 2013/0317372 A1 * | 11/2013 | Eberle | A61B 5/02154 600/478 |
| 2014/0058275 A1 * | 2/2014 | Gregorich | A61B 5/02154 600/485 |
| 2014/0180141 A1 * | 6/2014 | Millett | A61B 5/0215 29/857 |
| 2014/0248021 A1 * | 9/2014 | Belleville | A61B 5/02154 385/70 |
| 2015/0141854 A1 | 5/2015 | Eberle et al. | |
| 2017/0055908 A1 * | 3/2017 | Radman | A61B 5/0084 |

FOREIGN PATENT DOCUMENTS

| | | |
|---|---|---|
| WO | WO-2005041367 A1 | 5/2005 |
| WO | WO-2015013262 A1 | 1/2015 |
| WO | WO-2017062839 A1 | 4/2017 |

OTHER PUBLICATIONS

"International Application Serial No. PCT US2016 056098, International Preliminary Report on Patentability dated Apr. 19, 2018", 14 pgs.

"International Application Serial No. PCT/US2016/056098, International Search Report dated Mar. 20, 2017", 6 pgs.

"International Application Serial No. PCT/US2016/056098, Invitation to Pay Add'l Fees and Partial Search Report dated Jan. 8, 2017", 9 pgs.

"International Application Serial No. PCT/US2016/056098, Written Opinion dated Mar. 20, 2017", 12 pgs.

"Multimode optical fiber and pressure sensor", 1599.019PRV draft Oct. 6, 2015, (Oct. 6, 2015), 4 pgs.

Cibula, E., et al., "Miniature all-glass robust pressure sensor", (2009), 5098-5106.

Pinet, Eric, "Fabry-Perot Fiber-Optic Sensors for Physical Parameters Measurement in Challenging Conditions", Journal of Sensors, vol. 2009, Article ID 720980, (2009), 9 pgs.

Pinet, Eric, "Pressure measurement with fiber-optic sensors: Commerical technologies and applications", Proc. of SP{E, vol. 7753, (2011), 775304-1 to 775304-4.

Pinet, Eric, et al., "Ultra-miniature all-glass Fabry-Perot pressure sensor manufactured at the tip of a multimode optical fiber", Proc. of SPIE, vol. 6770, (2007), U1-U8.

* cited by examiner

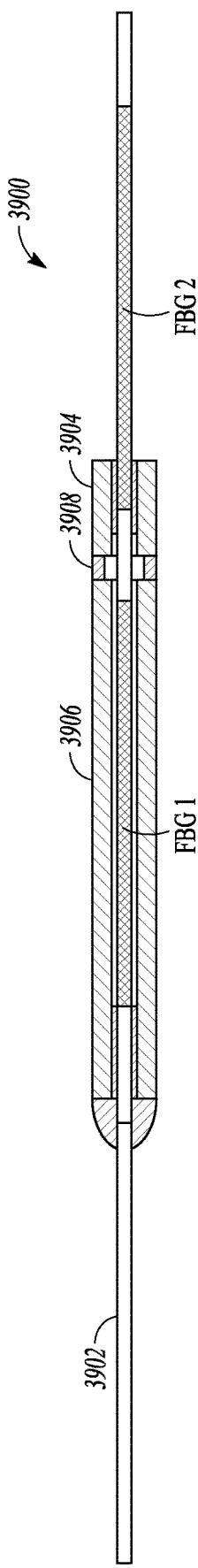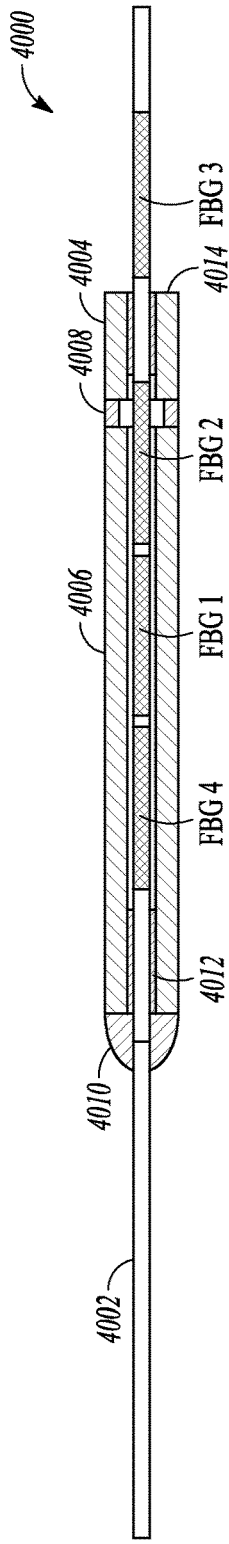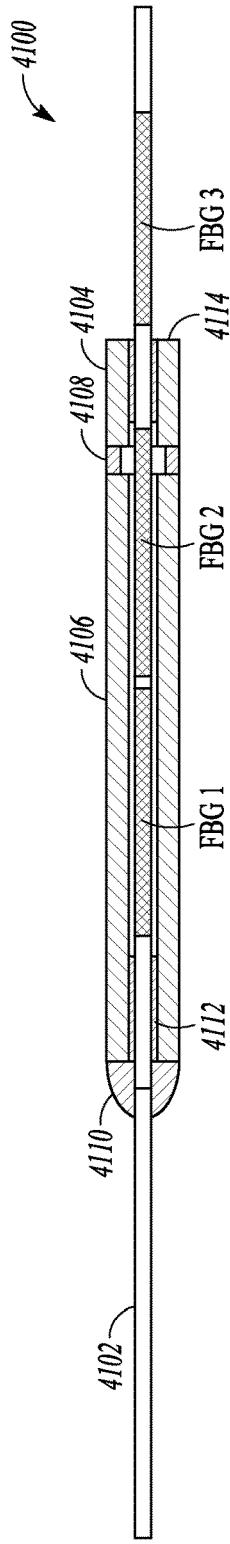

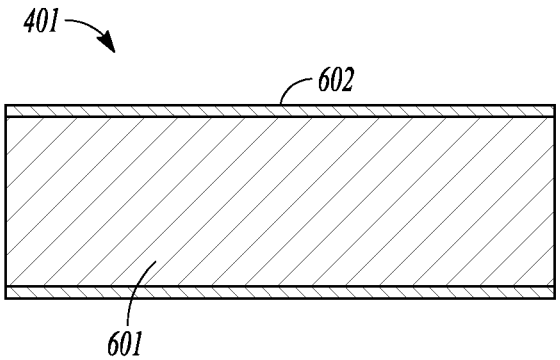 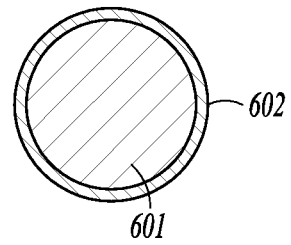
FIG. 10A    FIG. 10B
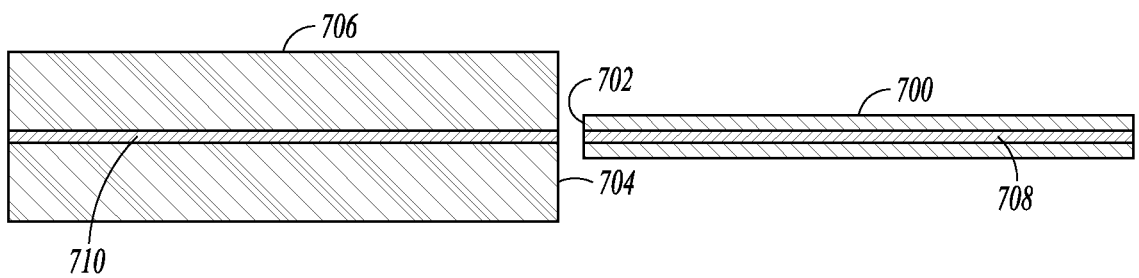
FIG. 11
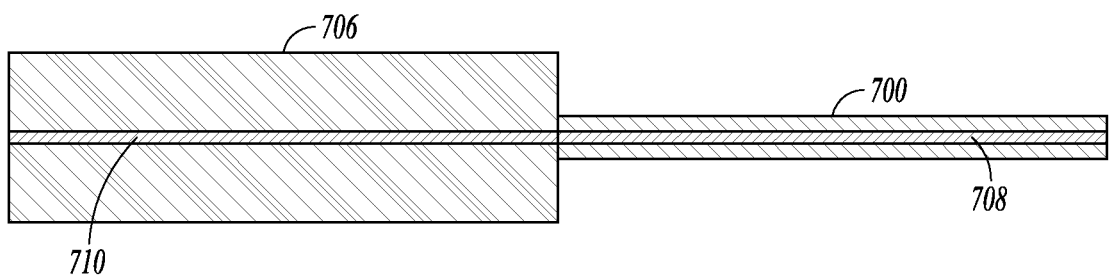
FIG. 12

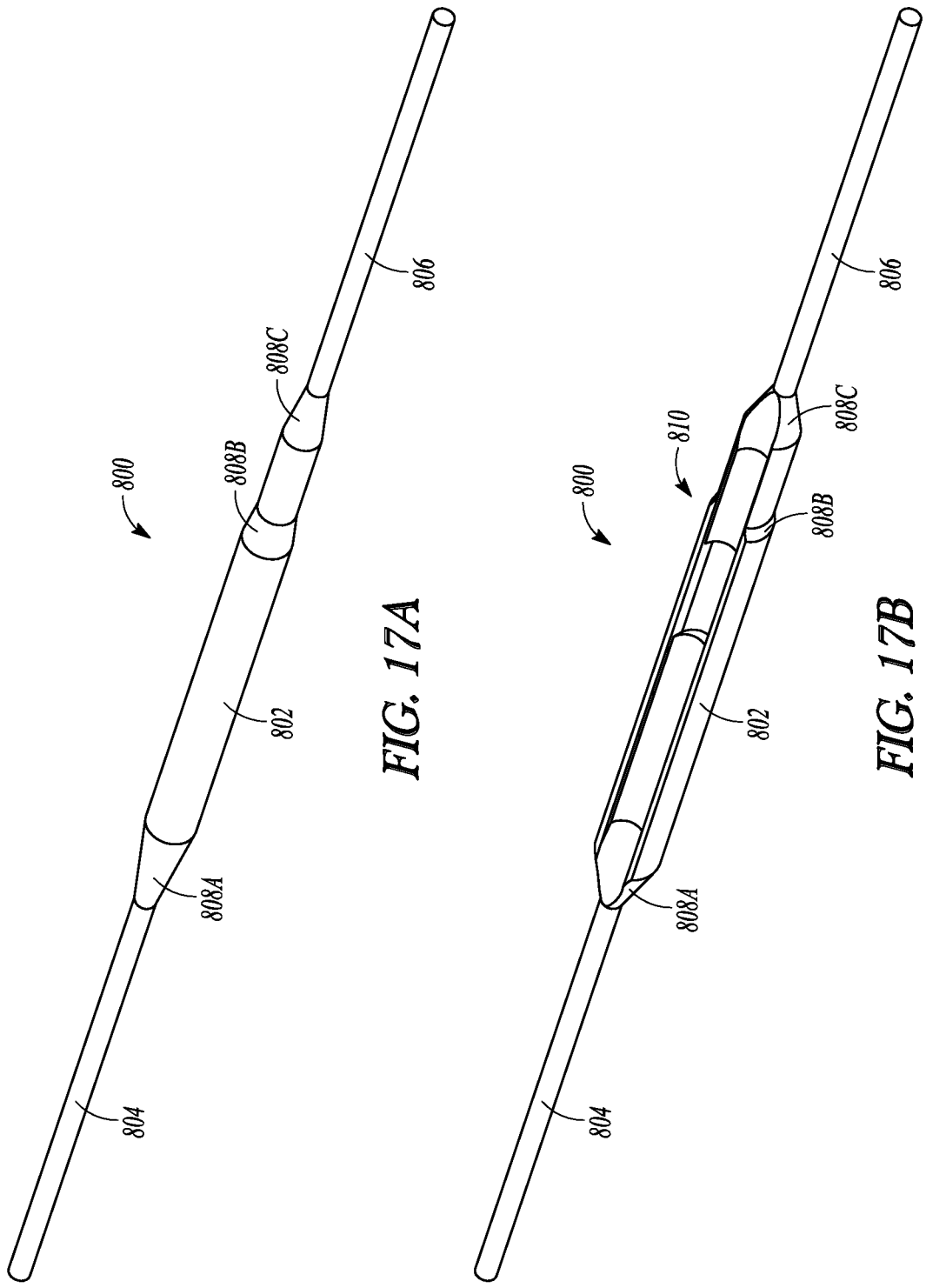

US 11,633,113 B2

OPTICAL SENSOR ASSEMBLIES AND METHODS

CLAIM OF PRIORITY

This application is a U.S. National Stage Filing under 35 U.S.C. 371 from International Application No. PCT/US2016/056098, filed on Oct. 7, 2016, and published as WO2017/062839 on Apr. 13, 2017, which claims the benefit of priority of U.S. Provisional Patent Application Ser. No. 62/239,624 to Eberle et al. and filed on Oct. 9, 2015; the benefit of priority of each of which is hereby claimed herein, and which applications and publication are hereby incorporated herein by reference in their entirety.

TECHNICAL FIELD

This document pertains generally to pressure sensing devices, imaging devices and methods and, in particular, to pressure sensing devices, imaging devices and methods using optical elements and techniques.

BACKGROUND

Before or during an invasive medical procedure, it can be desirable for a clinician, e.g., a physician, to take one or more pressure measurements from within a body lumen of a patient, e.g., a blood vessel, such as an artery or vein. For example, before implanting a stent at the site of an occlusion in a blood vessel, it can be desirable to determine the physiologic effect of the occlusion on the patient before making a decision whether to implant the stent. Furthermore, it can also be advantageous to measure the physiologic result of the stent implantation to ensure that the occlusion has been relieved.

One way to determine the effect of the occlusion on the patient is to measure the drop in blood pressure across the occlusion, such as using a Fractional Flow Reserve (FFR) technique, an Instantaneous Wave-Free Ratio (iFR) technique, a Post-Interventional Peripheral FFR (pFFR) technique and others. Generally speaking, according to data generated by long term studies using the FFR technique, if there is more than a 20-25% drop in pressure across the occlusion during maximum blood flow, the patient can be considered a candidate for coronary stent implantation. Otherwise, it can be preferable to treat the patient with a pharmaceutical regimen rather than implant a stent. Occlusions that look visibly similar, using an intravascular or other imaging modality, can be vastly different in terms of pressure drop across the occlusion. Therefore, an accurate measurement of pressure drop across an occlusion may help to tease out those occlusions that should be treated using a stent from those occlusions that are adequately treated by a pharmaceutical regimen.

Overview

In some examples, this disclosure is directed to an optical connector comprising a first optical fiber having a first diameter and having a core that includes a thermally expanded core portion adjacent a first end of the first optical fiber; a second optical fiber spliced to a second end of the first optical fiber, the second optical fiber having a second diameter less than the first diameter; and a connector bore having a first bore portion configured to receive the first end of the first optical fiber.

In other examples this disclosure is directed to a method of manufacturing a connector, the method comprising fusion splicing an end of a first optical fiber having a first diameter to an end of a second optical fiber having a second diameter less than the first diameter; thermally expanding a portion of a core of the first optical fiber; and inserting the first optical fiber into a bore of a first portion of the connector and inserting a third optical fiber into a bore of a second portion of the connector, wherein the third optical fiber includes an expanded core portion configured to at least partially align with the thermally expanded portion of the core of the first optical fiber.

In some examples, this disclosure is directed to a method of manufacturing a connector, the method comprising fusion splicing an end of a first optical fiber having a first diameter to an end of a second optical fiber having a second diameter less than the first diameter; thermally expanding a portion of a core of the first optical fiber; cleaving the first optical fiber through the thermally expanded portion into a first optical fiber portion and a second optical fiber portion; inserting the first optical fiber portion into a bore of a ceramic ferrule of a first portion of the connector and inserting the second optical fiber portion into a bore of a ceramic ferrule of a second portion of the connector; polishing at least one of an end of the first optical fiber portion and an end of the second optical fiber portion; and applying an anti-reflection coating to at least one of an end of the first optical fiber portion and an end of the second optical fiber portion.

In other examples this disclosure is directed to an apparatus comprising: an elongated assembly, at least a portion of which is sized, shaped, or otherwise configured to be inserted into a human body to measure a physiological parameter at an internal location within the body, wherein the elongated assembly includes: a guidewire having a length; and a multimode optical fiber, extending longitudinally along the guidewire, the optical fiber configured to communicate light between a location outside of the body and a portion of the optical fiber that is to be located at or near the internal location within the body at which the physiological parameter is to be measured, the optical fiber having a diameter of less than 50 micrometers.

In some examples, this disclosure is directed to an apparatus comprising: an elongated assembly, at least a portion of which is sized, shaped, or otherwise configured to be inserted into a human body to measure a physiological parameter at an internal location within the body, wherein the elongated assembly includes: a guidewire having a length; and a multimode optical fiber extending longitudinally along the guidewire, the optical fiber configured to communicate light between a location outside of the body and a portion of the optical fiber that is to be located at or near the internal location within the body at which the physiological parameter is to be measured, the optical fiber having a diameter of less than 50 micrometers; a pressure sensor assembly attached to a distal end region of the optical fiber, the pressure sensor assembly including: at least one tubular member having an inner diameter and configured to be bonded to and extend beyond a distal end of the optical fiber; a diaphragm bonded to a distal end of the tubular member and configured to respond to a change in pressure, wherein the diaphragm, the optical fiber and the inner diameter of the tubular member define a cavity adjacent the distal end of the optical fiber.

In other examples, this disclosure is directed to an apparatus comprising: an elongated assembly, at least a portion of which is sized, shaped, or otherwise configured to be inserted into a human body to measure a physiological parameter at an internal location within the body, wherein the elongated assembly includes: a guidewire having a length; a pressure sensor housing coupled to the guidewire; an optical fiber extending longitudinally along the guidewire, the optical fiber configured to communicate light between a location outside of the body and a portion of the optical fiber that is to be located at or near the internal location within the body at which the physiological parameter is to be measured; a collar configured to be bonded to the pressure sensor housing and the optical fiber; and a pressure sensor assembly bonded to a distal end region of the optical fiber, the pressure sensor assembly positioned distal to and spaced apart from the collar, the pressure sensor assembly positioned within and spaced apart from the pressure sensor housing.

In some examples, this disclosure is directed to an apparatus comprising: an optical fiber; and an optical fiber sensor including at least one Fiber Bragg Grating (FBG), wherein the sensor is coupled to the optical fiber using solder glass.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5-7 depict examples of portions of various pressure sensor assemblies.

FIG. 10A is a side view of an example of a multimode optical fiber that can be used in conjunction with a sensor.

FIG. 10B is a cross-sectional view of the example optical fiber shown in FIG. 10A.

FIG. 11 is a cross-sectional view depicting an ultra reduced diameter optical fiber having an end prior to fusion splicing with an end of a standard diameter optical fiber.

FIG. 12 is a cross-sectional view depicting the ultra reduced diameter optical fiber of FIG. 11 fusion spliced with a standard diameter optical fiber.

FIGS. 17A-17B depict an example of a core wire that can be used in combination with an optical fiber pressure sensor.

DETAILED DESCRIPTION

Measurement of pressure in a blood vessel has been achieved by incorporating miniaturized pressure sensors into guidewires that are small enough to be steered through the lumen of the vessel without also causing an obstruction, which would significantly alter the blood flow and create false pressure readings. These guidewires are typically of the same size as the guidewires which are used to treat coronary lesions, for example 0.014" diameter.

Figure 1:
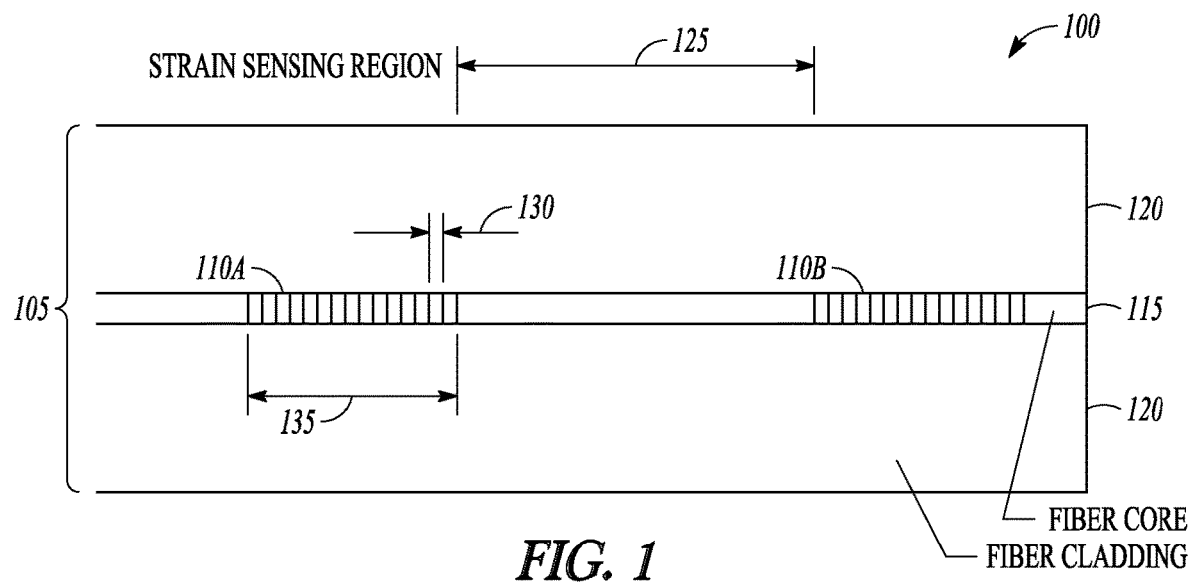
FIG. 1 is a cross-sectional side view illustrating generally, by way of example, but not by way of limitation, an example of an FBG pressure sensor in an optical fiber.

FIG. 1 is a cross-sectional side view illustrating generally, by way of example, but not by way of limitation, an example of a strain-detecting or pressure-detecting optical FBG sensor 100 in an optical fiber 105. The FBG sensor 100 can sense pressure received from a nearby area, and can transduce the received pressure into an optical signal within the optical fiber 105. The FBG sensor 100 can include Fiber Bragg gratings 100A-B in an optical fiber core 115, such as surrounded by an optical fiber cladding 120. The gratings 110A-B can be separated by a strain or pressure sensing region 125, which, in an example, can be about a millimeter in length. In an example, strain or pressure can be sensed, such as by detecting a variation in length of the optical path between these gratings 100A-B.

A Fiber Bragg Grating can be implemented as a periodic change in the optical refractive index of a selected axial portion of the optical fiber core 115. Light of specific wavelengths traveling down such a portion of the core 115 will be reflected. The period (distance or spacing) 130 of the periodic change in the optical index can determine the particular wavelengths of light that will be reflected. The degree of optical refractive index change and the axial length 135 of the grating 110A-B can determine the ratio of light reflected to that transmitted through the grating 110A-B.

Figure 2:
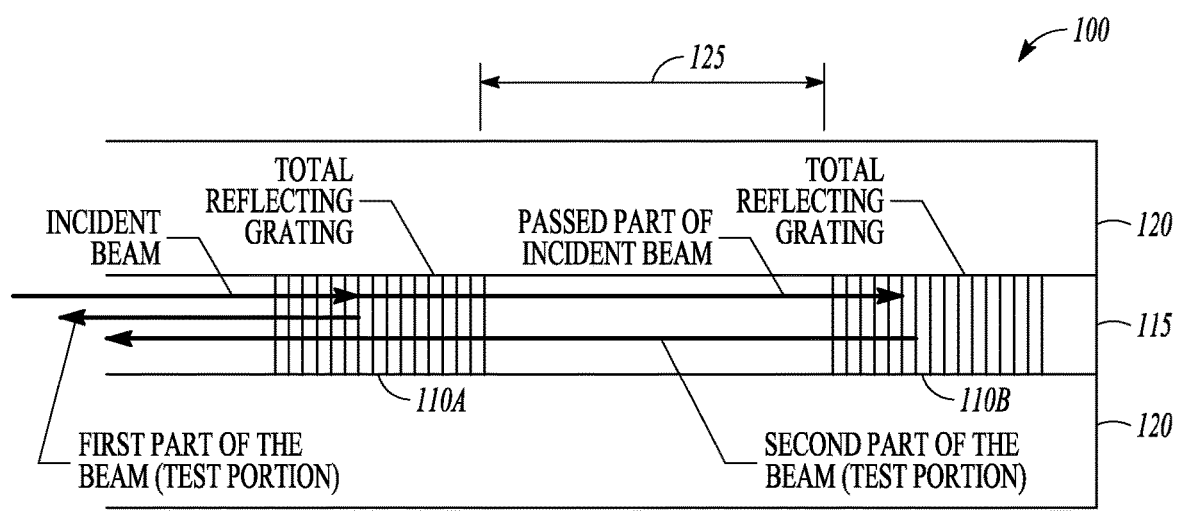
FIG. 2 is a cross-sectional side view illustrating generally, by way of example, but not by way of limitation, an example of an FBG grating interferometer sensor.

FIG. 2 is a cross-sectional side view illustrating generally, by way of example, but not by way of limitation, an operative example of an interferometric FBG sensor 100. The example of FIG. 2 can include two gratings 110A-B, which can act as mirrors that can both be partially reflective such as for a specific range of wavelengths of light passing through the fiber core 115. Generally, the reflectivity of each grating of a particular pair of gratings 110A-B will be substantially similar to the other grating in that particular pair of gratings 110A-B, but can differ between gratings of a particular pair of gratings 110A-B for particular implementations, or between different pairs of gratings 110A-B, or both. This interferometric arrangement of FBGs 110A-B can be used for discerning the "optical distance or optical pathlength" between FBGs 110A-B with extreme sensitivity. The "optical distance or pathlength" can be a function of the effective refractive index of the material of fiber core 115 as well as the physical distance 125 between FBGs 110A-B. Thus, a change in the refractive index can induce a change in optical path length, even though the physical distance 125 between FBGs 110A-B has not substantially changed.

An interferometer, such as can be provided by the FBG sensor 100, can be understood as a device that can measure the interference between light reflected from each of the partially reflective FBGs 110A-B. When the optical path length between the FBG gratings 110A-B is an exact integer multiple of the wavelength of the optical signal in the optical fiber core 115, then the light that passes through the FBG sensor 100 will be a maximum and the light reflected will be a minimum, such that the optical signal can be substantially fully transmitted through the FBG sensor 100. This addition or subtraction of grating-reflected light, with light being transmitted through the optical fiber core 115, can be conceptualized as interference. The occurrence of full transmission or minimum reflection can be called a "null" and can occur at a precise wavelength of light for a given optical path length. Measuring the wavelength at which this null occurs can yield an indication of the length of the optical path between the two partially reflective FBGs 110A-B. In such a manner, an interferometer, such as can be provided by the FBG optical fiber pressure sensor 100, can sense a small change in distance, such as a change in the optical distance 125 between FBGs 110A-B resulting from a received change in pressure. In this manner, one or more FBG sensors can be used to sense one or more pressures within a body lumen of a patient. This arrangement is an example of an FBG Fabry-Perot interferometer, which can be more particularly described as an Etalon, because the physical distance 125 between the FBGs 110A-B is substantially fixed.

The sensitivity of an interferometer, such as can be included in the FBG sensor 100, can depend in part on the steepness of the "skirt" of the null in the frequency response. The steepness of the skirt can be increased by increasing the reflectivity of the FBGs 110A-B, which also increases the "finesse" of the interferometer. Finesse can refer to a ratio of the spacing of the features of an interferometer to the width of those features. To provide more sensitivity, the finesse can be increased. The higher the finesse, the more resonant the cavity, e.g., two FBGs and the spacing therebetween. The present applicant has recognized, among other things, that increasing the finesse or steepness of the skirt of FBG sensor 100 can increase the sensitivity of the FBG sensor 100 to pressure within a particular wavelength range but can decrease the dynamic range of the FBG sensor 100. As such, keeping the wavelength of the optical sensing signal within the wavelength dynamic range of the FBG sensor 100 can be advantageous, such as to provide increased sensitivity to pressure. In an example, a closed-loop system can monitor a representative wavelength (e.g., the center wavelength of the skirt of the filtering FBG sensor 100). In response to such information, the closed-loop system can adjust the wavelength of an optical output laser to remain substantially close to the center of the skirt of the filter characteristic of the FBG sensor 100.

In an example, such as illustrated in FIG. 2, the interferometric FBG sensor 100 can cause interference between that portion of the optical beam that is reflected off the first reflective FBG 110A, e.g., highly reflective, with that reflected from the second reflective FBG 110B, e.g., highly reflective. The wavelength of light where an interferometric null will occur can be very sensitive to the "optical distance" between the two FBGs 110A-B. The interferometric FBG sensor 100 of FIG. 2 can provide another very practical advantage. In the example illustrated in FIG. 2, the two optical paths along the fiber core 115 are the same, except for the sensing region between FBGs 110A-B. This shared optical path can ensure that any optical changes in the shared portion of optical fiber 105 will have substantially no effect upon the interferometric signal; only the change in the sensing region 125 between FBGs 110A-110B is sensed. Additional information regarding FBG strain sensors can be found in U.S. Patent Application Publication No. 2010/0087732 to Eberle et al., which is incorporated herein by reference in its entirety, including its disclosure of FBGs and their applications.

Numerous example pressure sensor and guidewire configurations and pressure sensing configurations are disclosed in commonly assigned US Patent Application Publication No. 2015/0141854, the entire content of which being incorporated herein by reference.

In some example implementations, interferometric fiber optic pressure sensors can be formed using Fiber Bragg Gratings. In other example implementations, interferometric fiber optic pressure sensors can be formed that utilize a diaphragm that is responsive to pressure changes, instead of using Fiber Bragg Gratings. In general, but not exclusively, an interferometric fiber optic pressure sensor that utilizes Fiber Bragg Gratings can use a single mode optical fiber. In contrast, an interferometric fiber optic pressure sensor that utilizes a diaphragm instead of Fiber Bragg Gratings can use a multimode optical fiber.

In addition to being used with the FBG configurations, various techniques of this disclosure can also be applied to phase shift grating configurations, such as shown and described below with respect to FIGS. 4-7.

Figure 3A:
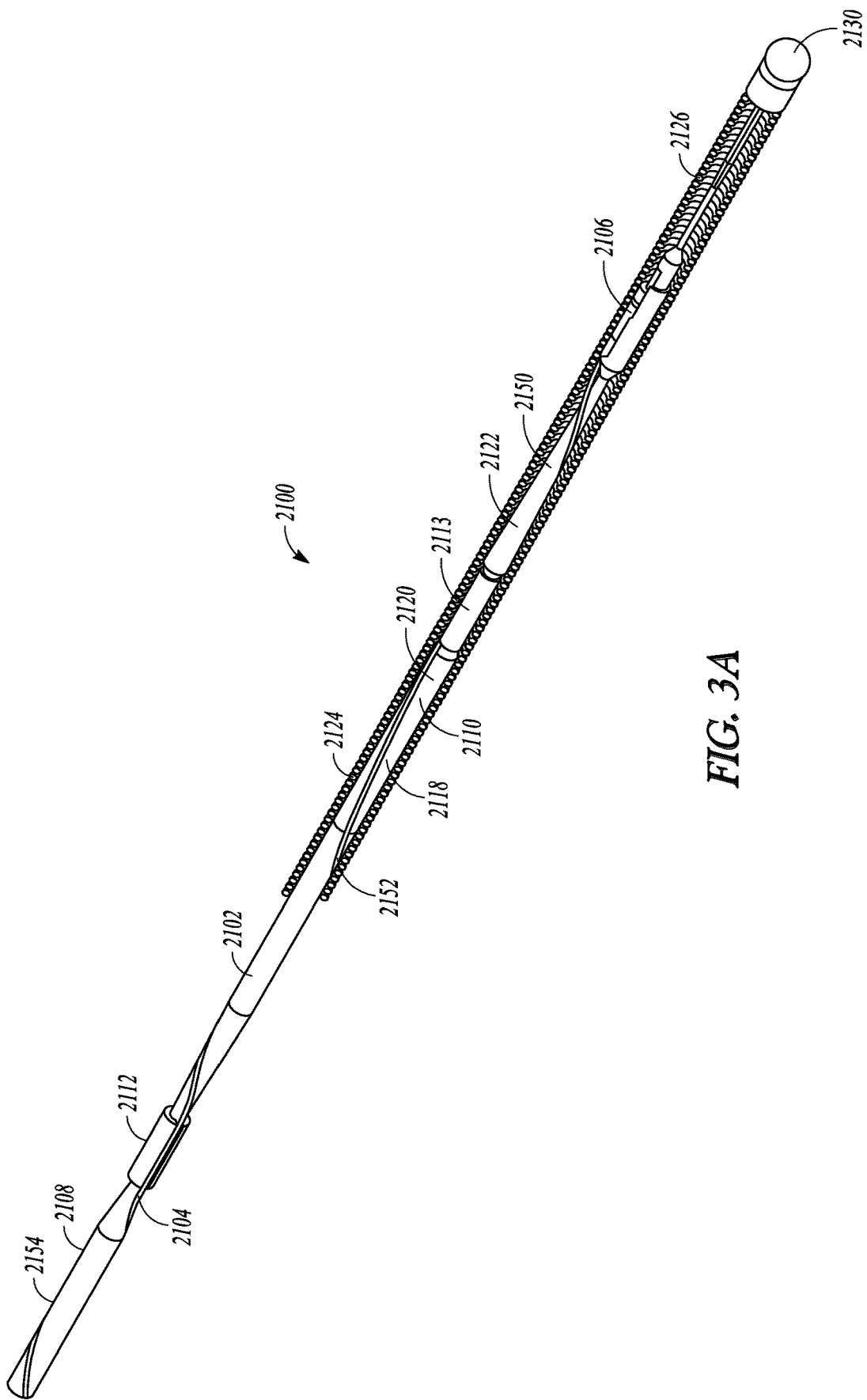
FIGS. 3A-3B depict various examples of a guidewire in combination with an optical fiber pressure sensor, in accordance with this disclosure.
Figure 3B:
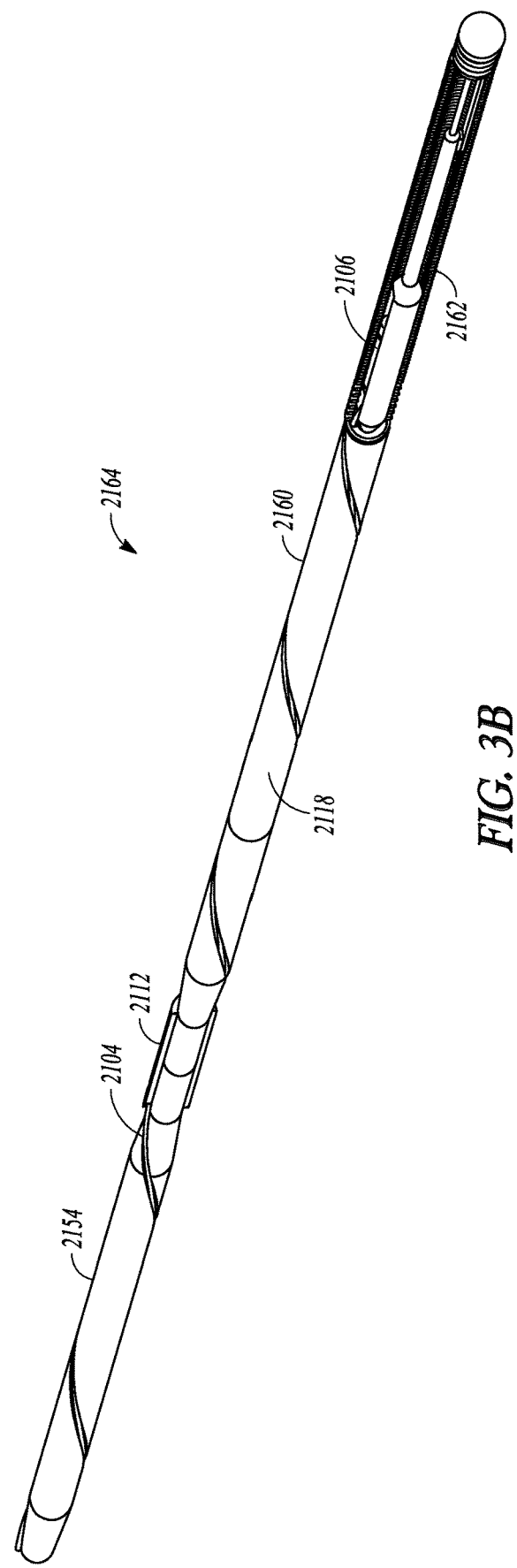

FIGS. 3A-3B depict various examples of a guidewire in combination with an optical fiber pressure sensor. FIG. 3A is an example of a partial cutaway view illustrating a combination 2100 of a guidewire 2102 and an optical fiber 2104 attached to an optical fiber pressure sensor 2106.

In one example, the guidewire 2102 can be substantially similar to the guidewire shown and described in U.S. Pat. No. 5,341,818 to Abrams et al. and assigned to Abbott Cardiovascular Systems, Inc. of Santa Clara, Calif., the entire contents of which being incorporated herein by reference. The guidewire 2102 can include a proximal portion 2108 and a distal portion 2110. The distal portion 2110 can be formed at least partially of superelastic materials. The guidewire 2102 can further include a tubular connector 2112 that can connect a distal end of the proximal portion 2108 and a proximal end of the distal portion 2110.

The tubular connector 2112 joining the proximal portion 2108 and the distal portion 2110 of the wire may be stainless steel (such as 304 series stainless steel) or nitinol material and may be grooved or slotted to accommodate the fiber. The groove or slot in the tubular connector 2112 may be aligned to the centerline of the tubular connector 2112 or it may be angled across the tubular connector 2112 to match the helix angle of the fiber groove path along the proximal or distal portions of the wire. The wire ends and the tubular connector 2112 may be adhesively joined, braze or solder attached to each other, the coupler may be welded to the wire end, or the tubular connector 2112 may be swaged or crimped onto the wire end.

In the case of a nitinol connector 2112, the connector 2112 can be expanded mechanically or by cooling it to martensite phase and deforming it. Once the nitinol connector 2112 has been expanded it can be installed over the wire and allowed to return to austenite phase, causing it to clamp down on the wire end.

The guidewire core material can affect the flexibility, support, steering and trackability of the guidewire while the guidewire core diameter can influence the flexibility, support, and torque of the guidewire. Suitable guidewire core materials can include the 18-8 stainless steels such as 304V, 304LV, and other 300 series alloys, nickel-based super alloys (such as, for example, MP35N), cobalt chromium molybdenum based super alloys, and nitinol.

Some examples of suitable metals and metal alloys that can be used to construct a guidewire include 304L and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL° 625. UNS: N06022 such as HASTELLOY® UNS: N10276 such as HASTELLOY® C276®, other HASTELLOY®, alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Stainless steel and superalloy materials provide excellent support, transmission of push force and torque characteristics but can be less flexible and more susceptible to kinking than nitinol. Nitinol can provide excellent flexibility and steering but can be less torqueable than stainless steel.

The guidewire core metal alloy materials can be subjected to thermomechanical processing to achieve the desired mechanical properties. To achieve the spring temper and ultimate tensile strength (for example, of greater than 300 ksi) desirable for the guidewire proximal shaft, the austenitic stainless steel 304V can be significantly cold worked (e.g. between 93 and 95% cold worked for UTS of 316 to 334 ksi). In wire form, 304V can gain tensile strength when stress relieved under a reducing atmosphere between 350 and 427 degrees Celsius. Nitinol wire can be cold worked (typically between 10 and 75%) during drawing and the amount of cold work in the wire prior to its final heat treatment (or shape set anneal) can dictate the ultimate tensile strength of the nitinol wire. The final heat treatment (or shape set anneal) for guidewires can be a straightening process performed under controlled time, temperature, and pressure conditions. The wire can be heat treated well above the austenite to martensite transformation temperature (450 to 600 C) while being subjected to longitudinal stresses to impart a straight memory to the wire. The shape set anneal process can define the final mechanical properties of the wire such as an ultimate yield strength of greater than 155 ksi.

Coupling different materials together to provide the best properties for each guidewire region can be a significant reason for choosing to join different wire sections together. The present inventors have also recognized that coupling different diameter wires together, whether those wires are the same material or different materials, can be advantageous. When the fiber groove is formed during the fiber draw processing or by other means into a constant diameter wire, coupling together two dissimilar diameter grooved wires can maintain the fiber groove sized appropriately for the fiber as the wire diameter is increased or decreased. An example is shown in FIG. 3A where a proximal connector 2112 joins a larger diameter stainless steel proximal shaft 2154 to a smaller diameter nitinol intermediate portion 2152 and a distal connector 2113 joins a small diameter stainless steel distal portion 2150 to the nitinol intermediate wire 2152.

In another example, when there is only a single joint between the proximal stainless steel shaft and a distal superelastic nitinol section that extends all the way to the distal tip, it can be desirable to either leave the region of the shapeable tip in the cold-worked or as-drawn condition so that shaping or permanent deformation of that region is possible when the physician intends to form the tip or to eliminate the superelasticity in the shapeable tip region by reversing the final strain anneal.

The coupled wire joints can be welded together rather than joined together using a tubular connector. This is relatively straightforward if the two wires are the same material but if they are dissimilar materials it is significantly more challenging. A laser based joining process can be used to directly melt the two wires to be joined or to melt a filler material at the joint. It can be desirable to optimize joints of stainless steel to nitinol to avoid the intermetallic phase rich in iron and titanium because Fe2Ti is a brittle intermetallic. A nickel or tantalum interlayer between the stainless steel and nitinol can be used to facilitate a laser weld join between these two materials.

Another laser joining process designed to form joints that are significantly smaller than the laser beam spot size can take advantage of heat accumulation at the joint interface. Laser irradiating one of the base materials (for example, the nitinol wire) and scanning toward the nitinol stainless steel interface with a laser power and speed such that the equilibrium temperature of the irradiated piece does not exceed its melt temperature (controlling the Gaussian laser spot to be the same diameter as the wires to be joined). Heat accumulation due to the thermal resistance of the interface can cause the temperature to rise above the melt temp of the nitinol as the laser beam approaches the interface, forming a molten layer. The laser beam can be turned off as it reaches the interface and the melt layer is quenched when it comes in contact with the adjacent cold work piece to form a seamless braze-like joint.

Combining a PTFE coated stainless steel proximal shaft with a superelastic nitinol distal portion via a tube coupler as described by FIG. 3A and their associated descriptions (or by directly joining the stainless steel shaft to the superelastic nitinol distal end) and employing the polymer sleeve or jacket as described above over the distal nitinol portion proximal of a cavity 2162 containing the sensor 2106 results in the optical fiber pressure sensor guidewire shown in FIG. 3B. The polymer sleeve or jacket 2160 can be coated with a durable hydrophilic coating, an intermediate coil can be deployed over the cavity 2162 with an uncoated radiopaque coil over the corewire distal of the cavity 2162 and sensor 2106. This guidewire sensor assembly 2164 can have the mechanical performance of a second generation high torque frontline guidewire with pressure sensing capability.

In some example configurations, the fiber pressure sensor assembly can include a flexible polymer jacket or sleeve over the tapered distal end of the guidewire core. As used in this disclosure, the term polymer, as used with regard to polymer coatings, is intended to be interpreted broadly and can include all polymers, prepolymers and the like that are suitable for use as a coating of a fiber pressure sensor assembly. A non-limiting list of suitable materials can include polyurethanes, including polyurethane thermoplastic elastomers; polyamides (nylons); polyethers; polyesters; polyacetals; acrylics; methacrylics; cellulosics; fluoroplastics; epoxies; keton-based resins and polymers; polyimide based resins and polymers; bismaleimides; nitriles; polyarylates; polycarbonates; liquid crystal polymers; terephthalate resins and polymers including polybutylene terephthalate and polyethylene terephthalate; polyetherimides; polyolefins including polyethylenes, polypropylenes, polybutylenes, polybutadienes; polyvinyls including polystyrenes and polyvinyl chlorides; elastomers especially thermoplastic elastomers; silicones; rubbers; ionomers; ceramers; dendritic polymers; and derivatives, copolvymers, multipolymers, blends and/or mixtures of any of the previous listed resins and polymers within each group and between each group, the latter including polyether block amide elastomers such as COPA and PEBAX.

The polymer sleeve or jacket covering the guidewire core between the proximal shaft the distal coil can provide a smoother surface and therefore greater lubricity than would a proximal coil disposed over that section, thereby allowing for smoother tracking through tortuous vasculature. The polymer sleeve or jacket may also be coated with, for example, a hydrophilic coating. The polymer sleeve or jacket may also cover coils, leaving the distal coil exposed provides better tactile feedback. The optical fiber may be positioned under (or within the wall thickness) the polymer sleeve or jacket as was described for routing the optical fiber along the pressure sensor assembly length covered by a proximal coil or a slotted flexible tube. Alternatively, a groove may be created (for example by lasing, by various mechanical means including scribing, a hot wire, etc. or depending on the polymer by thermally softening the sleeve or jacket as the fiber is wrapped into place) in the polymer sleeve or jacket to accommodate the fiber.

The guidewire 2102 can further include a core wire 2118 having an elongated portion 2120 and a tapered portion 2122 extending distally beyond the elongated portion 2120. In addition, the guidewire 2102 can include a proximal coil 2124 disposed about the elongated portion 2120 and a distal coil 2126 disposed about a portion of each of the elongated portion 2120 and the tapered portion 2122 and extending distally beyond the tapered portion 2122. In some examples, the proximal coil 2124 and the distal coil 2126 can be joined together via a mechanical joint. e.g., solder or adhesive. The guidewire 2102 can further include a distal plug 2130, about which a portion of the distal coil 2126 can be wound, or a conventional solder tip. Additional information regarding the components and construction of the guidewire 2102 can be found in U.S. Pat. No. 5,341,818.

Regarding construction of the combination 2100 of the guidewire 2102 and the optical fiber 2104 attached to an optical fiber pressure sensor 2106, in one example, a narrow, shallow channel or groove can be cut into the outer wall of the components that form the guidewire 2102, e.g., the core wire 2118 and the tubular connector 2112. The optical fiber 2104 can be positioned within the groove. Due to the relatively small dimensions of optical fiber 2104, the dimensions of the groove can have minimal impact on the performance of the guidewire 2102.

The groove can extend along the length of the guidewire 2102 substantially parallel to a longitudinal axis of the guidewire 2102. In another example, the groove can spiral about the guidewire 2102, e.g., a helically axially extending groove. In other examples, the groove can extend along a portion of the length of the guidewire 2102 substantially parallel to a longitudinal axis of the guidewire 2102 and then the groove can spiral about another portion of the length of the guidewire 2102, e.g., a helically axially extending groove. The pitch of the spiral can be varied along the length of the guidewire.

The groove can be fabricated using various techniques that include, but are not limited to, etching, machining, and laser ablation. In addition, the groove can be fabricated at various stages during the construction of the guidewire 2102, e.g., before or after applying a coating to the guidewire 2102.

The optical fiber 2104 can be bonded to the groove using various techniques. For example, the optical fiber 2104 can be bonded to the groove by applying a hot melt adhesive to the optical fiber 2104 prior to positioning the optical fiber 2104 in the groove and then subsequently applying heat.

In other examples, rather than a groove that is cut into the outer wall of the components that form the guidewire 2102, the guidewire 2102 can define a lumen (not depicted) that extends along a portion of the length of the guidewire 2102 substantially parallel to a longitudinal axis of the guidewire 2102. The lumen can be coaxial with the longitudinal axis of the guidewire 2102, or the lumen can be radially offset from the longitudinal axis of the guidewire 2102. The optical fiber 2104 can extend along the length of the guidewire 2102 through the lumen. The dimensions of the lumen can have minimal impact on the performance of the guidewire 2102.

In another example, the guidewire 2102 can be constructed to include an annular gap (not depicted) between the proximal coil 2124 and the elongated portion 2120. The optical fiber 2104 can then extend along the length of the elongated portion 2120 between an outer surface of the elongated portion 2120 and an inner surface of the proximal coil 2124. The optical fiber 2104 can be wound about the elongated portion 2120. In some examples, the optical fiber 2104 can be secured to the elongated portion 2120, e.g., via an adhesive.

The optical fiber pressure sensor 2106 can include the optical fiber 2104 that can be configured to transmit one or more optical sensing signals and a temperature compensated Fiber Bragg Grating (FBG) interferometer in optical communication with the optical fiber 2104. The FBG interferometer can be configured to receive pressure, e.g., from pressure waves, and to modulate, in response to the received pressure, the optical sensing signal.

The example of a pressure sensor 2106 of FIGS. 3A and 3B can further include FBGs (not depicted) similar to those described in detail above with respect to various examples of pressure sensors, e.g., FIG. 1, which can be used to sense changes in pressure. The FBGs can create a phase shift that can be tracked in a manner similar to that described above.

The techniques of this disclosure are not limited to the use of a single sensor in combination with a guidewire, e.g., guidewire 2102. Rather, two or more sensors, e.g., pressure sensors, can be combined with a guidewire by defining sensor regions in which each of the two or more sensors can function at a respective, unique wavelength and can be addressed accordingly by a laser matching the wavelength of the respective sensor. Each laser can be multiplexed onto the optical fiber using standard techniques, e.g., wavelength-division multiplexing (WDM), found in telecommunications systems.

By way of example, two pressure sensors can be positioned along the length of the guidewire 2102. By way of a further example, the two (or more) pressure sensors can be configured using a single fiber with each pressure sensor operating at a unique and separable wavelength. In yet another configuration, the incorporation of multiple pressure sensors can be achieved through integration of multiple optical fibers and sensors, each operational at the same wavelength of light or alternatively at more than one wavelength. Multiple optical fibers can be accommodated in various exemplary ways. The optical fibers can be placed in close proximity to each other along the length of the guidewire, or the optical fibers can be evenly or unevenly spaced around the circumference of the guidewire, such as in double or multiple helical formation or other winding patterns, or straight along the length of the guidewire. To accommodate the multiple optical fibers, the groove along the length of the guidewire can be widened, or separate grooves can be furnished around the circumference of the guidewire. Alternatively, a larger luminal bore can be made through the guidewire core.

In another example, the guidewire 2102 of FIGS. 3A and 3B can be combined with other sensor techniques. For example, the same guidewire can be used for both intravascular ultrasound (IVUS) imaging and pressure sensing by using the imaging sensor configurations described in U.S. Pat. No. 7,245,789 to Bates et al., and assigned to Vascular Imaging Corp, the entire contents of which being incorporate herein by reference. By way of specific example, one of the optical fibers in a 32 fiber arrangement can extend distally beyond an imaging sensor region, where an optical fiber pressure sensor, such as any of the optical fiber pressure sensors described in this disclosure, can be included that utilizes a different wavelength than that used by the imaging arrangement.

Figure 4:
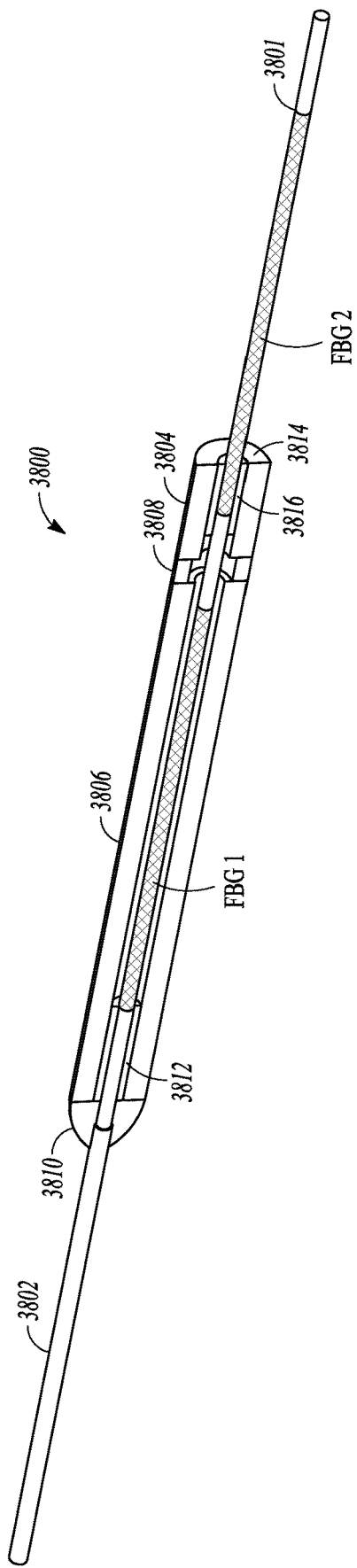
FIG. 4 depicts an example of a portion of a pressure sensor assembly.

FIG. 4 depicts another example of a portion of a pressure sensor assembly 3800. The pressure sensor assembly 3800 can include or be coupled to an optical fiber 3802, such as a reduced-diameter longitudinally extending central optical fiber 3802. The pressure sensor assembly 3800 can be located at or near a distal region of the optical fiber 3802.

The pressure sensor assembly 3800 can include a housing that includes a proximal housing portion 3806 and a distal housing portion 3804 separated by a window portion 3808. The proximal portion 3806 and the distal portion 3804 can be made from a hard, solid, or inelastic (e.g., fused silica) tubular or other housing. The window portion 3808 can be a soft, flexible, elastic, or compliant gasket located between the distal and proximal portions 3804, 3806 (e.g., silicone or polyurethane elastomer materials, pressure sensitive adhesive materials, or hot melt adhesive materials).

The optical fiber 3802 enters a proximal end 3810 of the proximal housing portion 3806 and can be securely captured, anchored, or affixed to the proximal housing portion 3806 via a tubular or other attachment (e.g., hardened epoxy or other adhesive) region 3812. Similarly, the optical fiber exits a distal end 3814 of the distal housing portion 3804 and can be securely captured, anchored, or affixed to the distal housing portion 3804 via a tubular or other attachment (e.g., hardened epoxy, solder glass, or other adhesive) region 3816.

In some example implementations, however, the optical fiber 3802 can enter a proximal end 3810 of the proximal housing portion 3806 and can be securely captured, anchored, or affixed to the proximal housing portion 3806 using solder glass bonding techniques. In some example implementations, the region 3816 can be fashioned using solder glass bonding techniques.

The pressure sensor assembly 3800 of FIG. 4 can further include a sensing region that can include two FBGs, namely FBG 1 and FBG 2. As seen in FIG. 4 an FBG, namely FBG 2, can extend distally beyond the distal end of the pressure sensor assembly 3800. By extending beyond the distal end of the pressure sensor assembly, the FBG 2 can be in direct contact with a bodily fluid, for example. In such an example configuration, any effect that securing materials, e.g., epoxies, may have on the FBG 2 can be eliminated.

In addition, by extending the FBG 2 beyond the distal end of the pressure sensor assembly 3800 instead of containing the FBG 2 within the housing, the length of the housing of the pressure sensor assembly 3800 can be reduced. In some example configurations, FBG 1 can be used to measure both pressure and temperature while FBG 2 can be configured to measure ambient temperature. e.g., of the bodily fluid, thereby providing an example of a temperature compensated pressure sensor. In one example configuration, it may be desirable to include a non-reflective termination 3801 as close to the distal end of the FBG 2 as possible. Without such a termination, a reflection can modulate the optical signal returning from the pressure sensor, which can affect the accuracy of the measurements.

FIGS. 5-7 depict examples of portions of various pressure sensor assemblies. Each of the various pressure sensor assemblies depicted in FIGS. 5-7 can include an FBG that extends distally beyond the distal end of each respective pressure sensor assemblies.

The example of a pressure sensor assembly depicted in FIG. 5 is similar to the pressure sensor assembly 3800 described above with respect to FIG. 4 and, as such, will not be described in detail again for purposes of conciseness. In some example configurations, each of FBG 1 and FBG 2 can include a phase shift, e.g., 90 degrees, in fringes at the center of the FBG. The phase shift can create a notch in the response, which can be tracked using a tracking circuit as described above.

It should be noted that, in some examples, the optical fibers of FIGS. 4-7 can enter a proximal end of a proximal housing portion and can be securely captured, anchored, or affixed to the proximal housing portion using solder glass bonding techniques. Similarly, the optical fibers of FIGS. 4-7 can enter a distal end of a distal housing portion and can be securely captured, anchored, or affixed to the proximal housing portion using solder glass bonding techniques.

FIG. 6 depicts an example of a pressure sensor assembly 4000 that can include four FBGs, namely FBGs 1-4. The pressure sensor assembly 4000 can include or be coupled to an optical fiber 4002, such as a reduced-diameter longitudinally extending central optical fiber 4002. The pressure sensor assembly 4000 can be located at or near a distal region of the optical fiber 4002.

The pressure sensor assembly 4000 can include a housing that includes a distal housing portion 4004 and a proximal housing portion 4006 separated by a window portion 4008. The distal portion 4004 and the proximal portion 4006 can be made from a hard, solid, or inelastic (e.g., fused silica) tubular or other housing. The window portion 4008 can be a soft, flexible, elastic, or compliant gasket located between the distal and proximal housing portions 4004, 4006.

The optical fiber 4002 enters a proximal end 4010 of the proximal housing portion 4006 and can be securely captured, anchored, or affixed to the proximal housing portion 4006 via a tubular or other attachment (e.g., hardened epoxy or other adhesive) region 4012. Similarly, the optical fiber 4002 exits a distal end 4014 of the distal housing portion 4004 and can be securely captured, anchored, or affixed to the distal housing portion 4004 via a tubular or other attachment (e.g., hardened epoxy or other adhesive) region 4016.

The pressure sensor assembly 4000 of FIG. 6 can further include a sensing region that can include four FBGs, namely FBGs 1-4. As seen in FIG. 6, an FBG, namely FBG 3, can extend distally beyond the distal end of the pressure sensor assembly 4000. By extending beyond the distal end of the pressure sensor assembly, the FBG 3 can be in direct contact with a bodily fluid, for example. In such an example configuration, any effect that securing materials, e.g., epoxies, may have on the FBG 3 can be eliminated. In addition, by extending the FBG 3 beyond the distal end of the pressure sensor assembly 4000 instead of containing the FBG 3 within the housing, the length of the housing of the pressure sensor assembly 4000 can be reduced.

In some example configurations, from left to right, FBG 4 can be used to measure pressure, FBG 1 can be used to measure temperature, FBG 2 can be used to measure pressure, and FBG 3 can be configured to measure ambient temperature, e.g., of the bodily fluid, thereby providing an example of a temperature compensated FBG interferometer in optical communication with the optical fiber 4002. Increasing the distance between the two temperature gratings, namely FBG 1 and FBG 3, increases the finesse, which can increase the sensitivity of the sensor, e.g., a steeper slope in the reflection band, and improve the quality factor.

FIG. 7 depicts an example of a pressure sensor assembly 4100 that can include three FBGs, namely FBGs 1-3. The pressure sensor assembly 4100 can include or be coupled to an optical fiber 4102, such as a reduced-diameter longitudinally extending central optical fiber 4102. The pressure sensor assembly 4000 can be located at or near a distal region of the optical fiber 4102.

The pressure sensor assembly 4100 can include a housing that includes a distal housing portion 4104 and a proximal housing portion 4106 separated by a window portion 4108. The distal housing portion 4104 and the proximal housing portion 4106 can be made from a hard, solid, or inelastic (e.g., fused silica) tubular or other housing. The window portion 4108 can be a soft, flexible, elastic, or compliant gasket located between the distal and proximal housing portions 4104, 4106.

The optical fiber 4102 enters a proximal end 4110 of the second housing portion 4106 and can be securely captured, anchored, or affixed to the second housing portion 4106 via a tubular or other attachment (e.g., hardened epoxy or other adhesive) region 4112. Similarly, the optical fiber exits a distal end 4114 of the first housing portion 4104 and can be securely captured, anchored, or affixed to the first housing portion 4104 via a tubular or other attachment (e.g., hardened epoxy or other adhesive) region 4116.

The pressure sensor assembly 4100 of FIG. 7 can further include a sensing region that can include three FBGs, namely FBGs 1-3. As seen in FIG. 7, an FBG, namely FBG 3, extends distally beyond the distal end of the pressure sensor assembly 4100. By extending beyond the distal end of the pressure sensor assembly, the FBG 3 can be in direct contact with a bodily fluid, for example. In such an example configuration, any effect that materials, e.g., epoxies, may have on the FBG 3 can be eliminated. In addition, by extending the FBG 3 beyond the distal end of the pressure sensor assembly 4100 instead of containing the FBG 3 within the housing, the length of the housing of the pressure sensor assembly 4100 can be reduced.

In some example configurations, one of the three FBGs can have a response that is larger than the response of the other two FBGs. For example, one of the FBGs, e.g., FBG 2, can have a response with about twice the bandwidth as either FBG 1 or FBG 3. FBG 1 and FBG 3 can each have a narrowband response that resonates with a different portion of the grating of FBG 2.

In one example, FBG 1 can be used to measure pressure, e.g., narrowband response, FBG 3 can be used to measure temperature, e.g., narrowband response, and FBG 2 can be used to measure pressure, e.g., broadband response. As described above, in order to generate a pressure signal that is ambient temperature compensated, the signal generated by FBG 3 can be used as a reference to null a shift in temperature. A controller circuit can be configured to control subtraction of the temperature reference signal (from FBG 3) from the pressure signals (from FBGs 1 and 2), such as to generate a temperature compensated pressure signal.

The present applicant has recognized, among other things, that the use of single mode fiber based pressure sensing techniques can be challenging due to the alignment requirements for connecting the optical fiber to a pressure measurement instrument. The present applicant has recognized that multimode optical fiber has a reduced alignment precision requirement due to the normally larger core diameter. The present applicant has recognized that the requirements of traditional fused silica based optical fibers, used for example in telecommunications applications, include the need for protective coatings to prevent breakage of the fiber, which can lead to a larger diameter for the fiber with the coating.

The present applicant has recognized that miniaturization of a multimode optical fiber and multimode optical fiber based pressure sensor present both a major challenge and a major advantage for incorporation into, for example, a frontline coronary guidewire, while minimizing the impact on the mechanical performance of the guidewire and improving the ability to connect the guidewire optically to the pressure measurement instrument. The present applicant has further recognized that certain optical fiber constructions based on materials other than fused silica, e.g., borosilicate glass, plastic and other materials, can be less susceptible to breakage, when constructed correctly, and can be utilized without a protective coating, which can enable a smaller diameter and can also simplify assembly processes.

Miniaturized optical fiber pressure sensing techniques have been demonstrated utilizing multimode optical fibers. Examples of these techniques can include pressure sensors based on white light interferometric effects using reflections from extrinsic diaphragms forming a pressure variable cavity. These sensors have been reduced in size to a diameter of approximately 125 micrometers (also referred to as "microns") using multimode optical fiber that is commonly used in telecommunications technology. For example, the multimode optical fiber may have a core diameter of approximately 62.5 micrometers and a cladding diameter of 125 micrometers. In some configurations, a reduced cladding multimode optical fiber may have a core diameter of approximately 50 micrometers and a cladding diameter of 80 micrometers.

The present applicant has recognized that ultra reduced diameter optical fiber can be advantageous to minimize the impact of the sensing technology on the mechanical properties of the guidewire. For example, a reduced cladding optical fiber, with a cladding diameter of 80 micrometers and a coating diameter of, for example, 100 micrometers, has a cross-sectional area of 7800 micrometers$^2$ which is about 8% of the cross-sectional area of a 0.014" diameter guidewire, which can be significant. By comparison, an ultra reduced cladding optical fiber with an outer diameter of 25 micrometers and without a coating has a cross-sectional area of about 490 micrometers$^2$, which is about 0.5% of the cross-sectional area of the same guidewire, and is insignificant since the manufacturing tolerances of the guidewire diameter are typically larger than 1%.

The present applicant has determined that an ultra reduced cladding multimode optical fiber with outer dimensions suitable for integration into a coronary guidewire, as described in this disclosure, can be achieved. For example, an optical fiber made from a borosilicate glass preform, sized to achieve a finished outer diameter of approximately 25 micrometers, can be infused with additional dopant materials in the outer layer or sleeved, for example, with a pure silica jacket. The dopant or sleeve techniques create the necessary difference in the refractive indices between the cladding and the core, and the thickness of the fiber outer diameter cladding layer can be, for example, approximately 1 micrometer, to achieve an optical fiber with a core diameter of approximately 23 micrometers and an ultra reduced cladding diameter of approximately 25 micrometers.

The infused or sleeved outer layer may be designed to achieve a thickness and refractive index that is suitable to create a waveguide for the operating wavelengths of the sensor, such as white light. The construction of the optical fiber can be modified to produce what is commonly known as a step index profile or other profiles such as a graded index.

The primarily borosilicate glass optical fiber in these dimensions can be relatively strong, with or without a coating, and may be handled with normal care while the fiber is being processed and incorporated into the guidewire. An optical fiber of these dimensions may be incorporated into a guidewire with the techniques described in this disclosure with minimal impact on the construction, thereby maintaining the mechanical characteristics of the guidewire. Advantageously, the optional elimination of a coating layer can aid in the processing of the fiber as selective stripping of the coating can be eliminated.

Furthermore, a smaller overall diameter fiber can lead to easier integration into a medical device, such as a frontline coronary guidewire, as the cross-sectional area is minimized and the structure of the guidewire is minimally affected, thereby maintaining the mechanical characteristics of the device. Other materials may be used which may or may not require a protective coating layer for handling, such as plastic optical fiber.

An ultra reduced cladding optical fiber with reduced core diameter, such as 23 micrometers, can function as a multimode fiber. The number of supported optical modes may be reduced compared to the number that a larger diameter core such as a 50 micrometers core can support. However, the alignment requirements for making an optical connection can be significantly reduced when compared to a single mode optical fiber, which may have a core diameter or mode field diameter on the order of 5 micrometers to 10 micrometers. Additionally and advantageously, the optical connection can be less sensitive to contamination, which may be present in the operating environment. These borosilicate multimode fibers can have a higher optical attenuation than a comparable fused silica fiber, but this may be unimportant in, for example, a medical application where short lengths of fiber are used, and the overall attenuation is not significant.

The present applicant has determined that an optical pressure sensor may be formed intrinsically or extrinsically in or on the above mentioned ultra reduced cladding multimode fiber. For example, in FIG. 4 below, an extrinsic pre-assembled sensor form may be attached to the distal end of the ultra reduced cladding multimode optical fiber.

Figure 8:
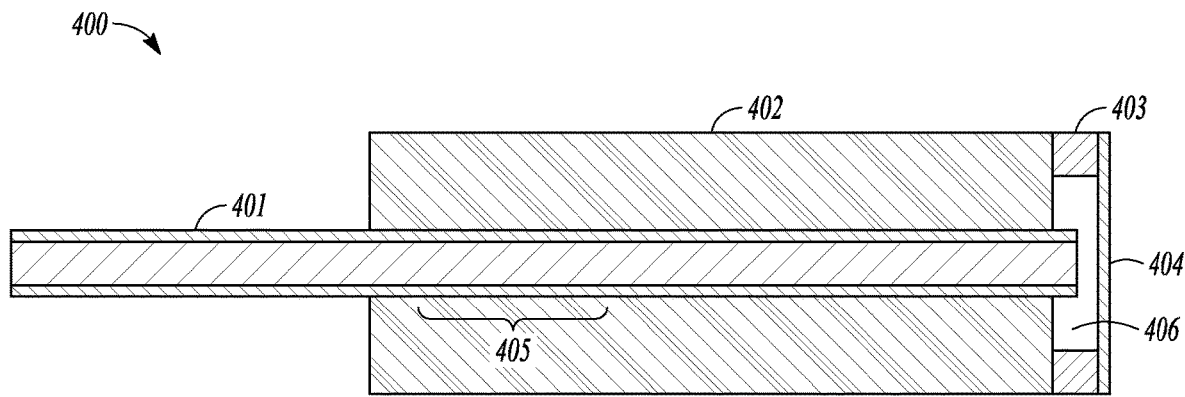
FIG. 8 depicts an example of a sensor assembly using a multimode optical fiber, in accordance with various techniques of this disclosure.

FIG. 8 shows an example of a sensor assembly 400 in accordance with various techniques of this disclosure. FIG. 8 depicts an extrinsic sensor form 400 that can be attached to the distal end of the ultra reduced cladding multimode optical fiber 401. The sensor form 400 can be made from various materials and various assembly and bonding techniques can be used. In some example configurations, these materials can be inexpensive and can have similar thermal properties to the optical fiber 401. Example materials can include glass, such as silica or borosilicate, silicon or other suitable materials. In some example implementations, the sensor assembly 400 can be pre-assembled. In other example implementations, rather than being pre-assembled, the sensor assembly 400 can be assembled on the fiber.

In the example shown in FIG. 8, tubular member 403 can be bonded to tubular member 402 and diaphragm 404 through suitable bonding techniques such as fusion bonding, electrostatic bonding, epoxy bonding, solder glass bonding, and other known techniques. The diaphragm 404, rather than any FBGs, can be used to sense any pressure changes in the sensor assembly 400. Other methods of construction of the sensor assembly can be employed. For example, the assembly can be made in one piece by creation from bulk material using 3 dimensional laser fabrication techniques. The diaphragm may be planar or may contain shapes that can alter or enhance the mechanical performance of the diaphragm, such as a concentric dot or ring, as described in U.S. Pat. No. 8,752,435, and incorporated herein by reference.

The sensor assembly 400 can be bonded to optical fiber 401 through various or similar techniques in the region 405. By way of example, a $CO_2$ laser may be precisely focused in region 405 to create a heated zone where fusion bonding may be accomplished in an air or vacuum environment. Optical fiber 401 can have dimensions suitable for the intended final use. For example, to minimize impact of the optical fiber on the mechanical characteristics of the device, such as a coronary guidewire, the outer diameter may be less than 50 micrometers, such as 25 micrometers, and the length may be 195 centimeters for use in a coronary guidewire as described earlier.

Tubular member 402 can be cylindrical or another suitable shape, and can have an outer diameter of 125 micrometers or less, for example, and an inner diameter sized to accommodate optical fiber 401, for example 25.5 micrometers. Tubular member 402 can be as short or as long as necessary for suitable mounting in, for example, the coronary guidewire.

The mounting technique can include a cantilever technique for isolation of the sensor from mechanical forces on the guidewire. Tubular member 403 can be of similar dimensions to 402. For example, the outer diameter can be 125 micrometers and the inner diameter may be, for example, 100 micrometers, thereby creating a suitably dimensioned cavity 406 and allowing sufficient flexibility for diaphragm 404.

Diaphragm 404 can be formed of a suitable material, such as silicon or glass. A silicon diaphragm can be formed from a silicon wafer by utilizing standard silicon wafer preparation techniques, such as polishing or electrochemical etching of a thicker wafer through etch stop techniques using polysilicon or epitaxial silicon layers, for example. The diaphragm outline can be achieved through chemical or laser etching of the silicon wafer at various stages of the process. The thickness of diaphragm 404 can be of the order of a few microns, e.g., less than 5 micrometers, in order to achieve the desirable sensitivity of the sensor in the intended use. Components 401, 402, 403, 404 and 405 when assembled, can form a sealed cavity 406 which may be filled with a suitable gas or vacuum.

The sensor assembly 400 can be combined in a guidewire, e.g., many of the guidewire designs described in commonly assigned US Patent Application Publication No. 2015/0141854, the entire content of which being incorporated herein by reference. For example, the sensor assembly 400 can be combined with a guidewire including a core wire defining a cradle, e.g., such as shown in FIG. 45B of US Patent Application Publication No. 2015/0141854. The resulting combination can be similar to the combination shown in FIG. 46A of US Patent Application Publication No. 2015/0141854, with the pressure sensor assembly 4600 replaced by the sensor assembly 400 of FIG. 8.

During a procedure, a force can be exerted on the optical fiber and the optical fiber can be pulled, and/or a core wire ofa guidewire can be moved. The present applicant has recognized that, due to the miniaturization of these components, a stress on the fiber and/or a movement of the core wire can be communicated to the sensor, resulting in the sensor detecting a pressure change. As described below with respect to FIG. 9, the present applicant has recognized that the pressure sensor can be physically and mechanically isolated from mechanical stresses in the guidewire and the flexible optical fiber, which can improve the pressure measurement accuracy of the assembly.

Figure 9:
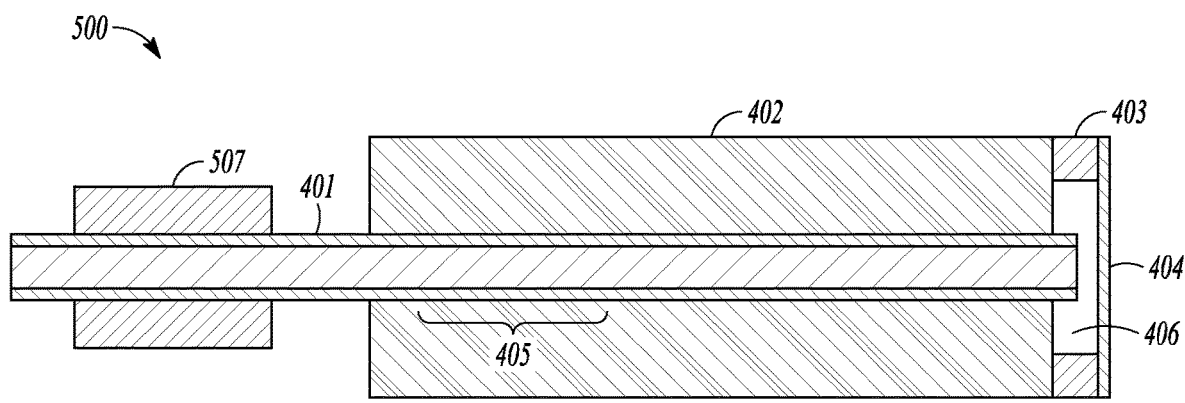
FIG. 9 depicts another example of a sensor assembly using a multimode optical fiber, in accordance with this disclosure.

FIG. 9 shows another example of a sensor assembly 500, which can be an alternative arrangement of sensor assembly 500. The sensor assembly 500 can also be combined with a guidewire. For example, the sensor assembly 500 can be combined with a guidewire including a core wire defining a cradle (or pressure sensor housing), e.g., as shown in FIG. 45B of US Patent Application Publication No. 2015/0141854. The resulting combination can be similar to the combination shown in FIG. 46A of US Patent Application Publication No. 2015/0141854, with the pressure sensor assembly 4600 replaced by the sensor assembly 500 of FIG. 9.

Assembly 500 can include an additional component 507, e.g., a collar, that can be attached to optical fiber 401 proximal to the sensor in order to physically and mechanically isolate the sensor assembly 500 from mechanical stresses in the guidewire and the flexible optical fiber. Collar 507 can be formed from fused silica or borosilicate glass or another suitable material. Collar 507 can be cylindrical or another shape that allows attachment to optical fiber 401 by fusion, epoxy bonding, solder glass bonding, or other suitable methods. By way of example, collar 507 can be a cylindrical tube made from borosilicate glass that can be fusion bonded to optical fiber 401. Collar 507 can be utilized as a mounting and isolation apparatus and can be used in other pressure sensor examples described in this disclosure.

Assembly 500 can be attached to the distal end of a guidewire by affixing collar 507 to a pressure sensor housing. By way of specific example, the sensor assembly 500 can be positioned within the cavity defined by the pressure sensor housing 4610, e.g., see FIG. 46A of US Patent Application Publication No. 2015/0141854. The collar 507 can be bonded to the housing 4610, without any of the other structures of the assembly 500 that are distal to the collar 507 contacting the housing 4610. Because the collar 507 can be bonded to the pressure sensor housing proximal to and spaced apart from the pressure sensor, movement and/or stresses will not be communicated to the pressure sensor due to the gap between the collar 507 and the tubular member 402 of the pressure sensor.

In this manner, the remaining structures of the assembly 500 can be physically and mechanically isolated from the sensor housing through this mounting method by allowing a suitable clearance gap around them, thereby isolating the pressure sensor from mechanical stresses in the guidewire and the flexible optical fiber. Thus, the sensitive diaphragm and distal end of the sensor can attain accurate measurements of the surrounding fluid pressure without influence of environmental motion. This scheme can be applied to any of the sensor configurations of US Patent Application Publication No. 2015/0141854, as appropriate.

FIGS. 10A and 10B show an example of an ultra reduced cladding multimode optical fiber 401 suitable for the implementation of the sensor scheme. FIG. 10A is a side view of the multimode optical fiber 401 and FIG. 10B is a cross-sectional view of the multimode optical fiber 401. Various configurations of the fiber can be achieved. In an example configuration, the cladding 602 of the optical fiber 401 may be made from a relatively thin layer of fused silica glass, which can surround a relatively large core material 601 made from borosilicate glass.

The dimensions of the optical fiber 401 and the refractive indices of the materials can vary depending on the wavelengths of light chosen and the application of the optical sensor. Example dimensions for an optical fiber suitable for incorporation into a coronary guidewire can be 22.3 micrometers diameter for the borosilicate glass and 25 micrometers outer diameter for the fused silica cladding. e.g., 22.3/25 core/cladding. Other examples dimensions (in micrometers) include 26.8/30, 33.9/38, 44.6/50 and other combinations of dimensions. A protective coating layer can also be applied to the outside of the optical fiber. Alternatively, the coating can be a suitable adhesive material or thermoplastic that can be utilized to attach the optical fiber to the guidewire assembly.

In addition to the techniques described above, this disclosure is directed to techniques for manufacturing a proximal connector in a sensing and/or imaging guidewire. A "smart" guidewire can be connected to a monitoring system by means of a "system lead." The system lead, in general, can include a ruggedized fiber optic tail with a connector that is inserted into the monitoring interface of the system console and a demountable connector into which the guidewire part of the assembly can be inserted.

In a current design, the demountable wire connector desirably has mechanical precision of alignment that is suitable for a single-mode optical fiber. To attain an acceptable optical insertion loss, the mechanical misalignment of the optical fiber cores on each side of the interface can be a small fraction of the optical mode size. If the mode size is 6 microns ($\mu$m), for example, then the alignment should be accurate to approximately 1 $\mu$m for relatively low insertion loss.

The connection is desirably reasonably robust with respect to contamination as there is likely to be some intrusion by fluids during the procedure, even with careful cleaning and handling of the device. If any contamination were to settle on the optical core region of either fiber, and this contamination were of appreciable size. e.g., several microns, then it could also block a significant part of the optical throughput. Standard optical connectors, such as those used in telecommunication products, have the desired mechanical precision but they are not easily scaled to the size required in this application. For instance, the smallest standard ceramic ferrules available today might have an outer diameter of 1.25 millimeter (mm) and inner diameter hole of 80 $\mu$m. Because standard sized therapeutic catheters should be threaded over the guidewire, the ferrule cannot exceed the standard dimension of the guidewire, which is approximately 350 $\mu$m.

It has been shown that it is possible to make the ferrule with an outer diameter of 350 µm, but it has been difficult to fabricate the inner diameter any smaller than 125 µm. A guidewire in accordance with various techniques of this disclosure can use an optical fiber having a 25 µm inner diameter, which can require a workaround such as buffering the fiber up to 125 µm with a very high tolerance capillary. This workaround, however, can be costly and difficult in any volume of production. In addition, manufacturing the means of holding the two ends in alignment, which can be achieved by a precision split sleeve, can be challenging.

The present inventors have developed an improved technique for manufacturing a proximal connector in a sensing and/or imaging guidewire that can address, among other things, the challenges of 1) mechanical tolerance of the optical connection and 2) resistance of optical connection to contamination. As described below with respect to FIGS. 11-15, an improved technique for manufacturing a proximal connector in a sensing and/or imaging guidewire can include fusion splicing the ultra-reduced diameter fiber. e.g., 25 µm fiber, to a standard diameter fiber, e.g., 125 µm fiber, thermally expanding the core in the standard diameter fiber, cleaving or cutting into two parts the standard diameter fiber in the region of the thermally expanded core, inserting the two parts into ceramic ferrules, and then optical polishing the faces of the optical fiber. Alternatively the thermal expansion and/or cleaving may be achieved prior to fusion splicing.

FIG. 11 is a cross-sectional view depicting an ultra reduced diameter optical fiber 700 having an end 702 prior to fusion splicing with an end 704 of a standard diameter optical fiber 706. The optical fiber 700 has a core 708 and the optical fiber 706 has a core 710.

It should be noted that although some of the configurations shown depict a single mode example configuration, similar techniques can be applied to ultra reduced multimode fiber designs, assuming that that the outer diameter of the multimode fiber is larger to begin with. As an example, a 23 micrometer core can be expanded to a larger diameter.

FIG. 12 is a cross-sectional view depicting the ultra reduced diameter optical fiber 700 of FIG. 11 fusion spliced with the standard diameter optical fiber 706. As seen in FIG. 12, the cores 708, 710 are generally in alignment. The large relative size mismatch between the ultra reduced diameter optical fiber 700 and the standard diameter optical fiber 706, as well as the very small fiber size of the ultra reduced diameter optical fiber 700, have been problematic for traditional plasma arc fusion splicers. In accordance with this disclosure, fusion technologies such as $CO_2$ laser heating, for example, can be used to fuse the end 702 of the ultra reduced diameter optical fiber, e.g., 25 µm fiber, to the end 704 of the standard 1251 µm fiber.

Figure 13:
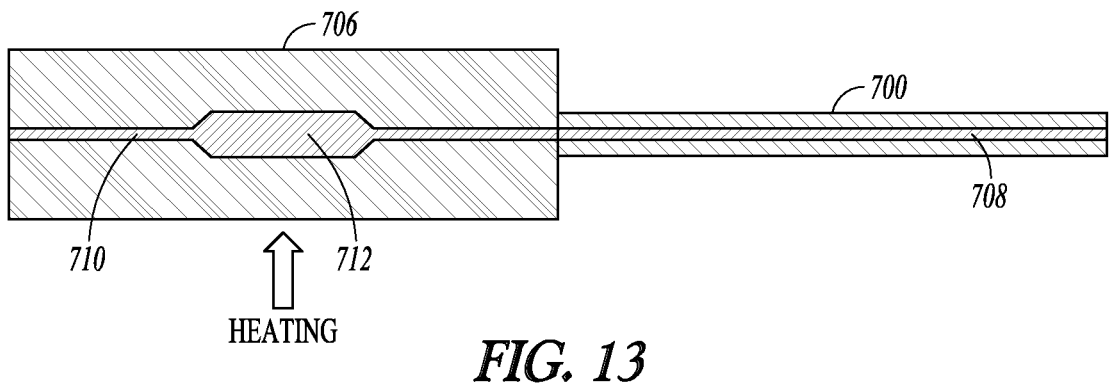
FIG. 13 is a cross-sectional view depicting a thermal expansion of the fiber core of the standard diameter optical fiber.

FIG. 13 is a cross-sectional view depicting a thermal expansion of the fiber core of the standard diameter optical fiber. As seen in FIG. 13, heating equipment can apply heat to at least a portion 712 of the core 710 of the standard diameter optical fiber 706. In some example configurations, the heating equipment can be the same equipment used for the fusion splicing, e.g., a $CO_2$ laser. In other example configurations, it could also be a heated filament or plasma arc between electrodes.

The typical temperature for this operation would be many hundreds of degrees Celsius, but would be below the glass softening temperature of the host fiber. An example of the glass softening temperature for a silica optical fiber can be around 1600° C. The time taken for the mode expansion can be related to the temperature and the constituent dopants present in the fiber. The operation can be achieved in a relatively short amount of time (<1 minute) or over a much longer time (hours), depending on the amount of control required in the final result. The expansion can be monitored by observing the temperature profile of the fiber in the infrared region from a side view, sometimes referred to as a 'Hot View' in fiber splicing terminology. It can also be monitored from the end by used of an optical camera sensitive to the wavelength of light being launched into the fiber.

An advantage of the thermally expanded core portion 712 is that the optical mode size can also increase as the dopants present in the core region migrate outwards. This can be used to expand the core, e.g., from 6 µm to 20 µm. The expanded mode size can mean any mechanical misalignment of the optical cores will result in much lower optical insertion loss. In addition, the larger mode size can also be useful in making the optical loss more robust with respect to contamination between the faces of the optical connection. As the optical mode is spread over a much larger surface area, any contamination can have less effect on the optical insertion loss than with the smaller mode size.

Figure 14:
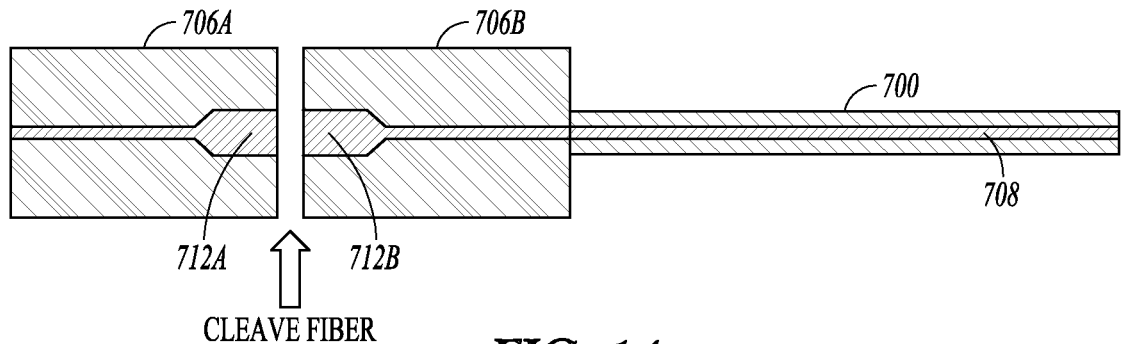
FIG. 14 is a cross-sectional view depicting a thermally expanded fiber core of the standard diameter optical fiber cleaved into two portions.

FIG. 14 is a cross-sectional view depicting a thermally expanded fiber core of the standard diameter optical fiber cleaved into two portions. As seen in FIG. 14, the optical fiber 706 can be cleaved into two portions at the thermally expanded core portion 712, resulting in optical fiber portions 706A, 706B including expanded core portions 712A, 712B, respectively.

Figure 15:
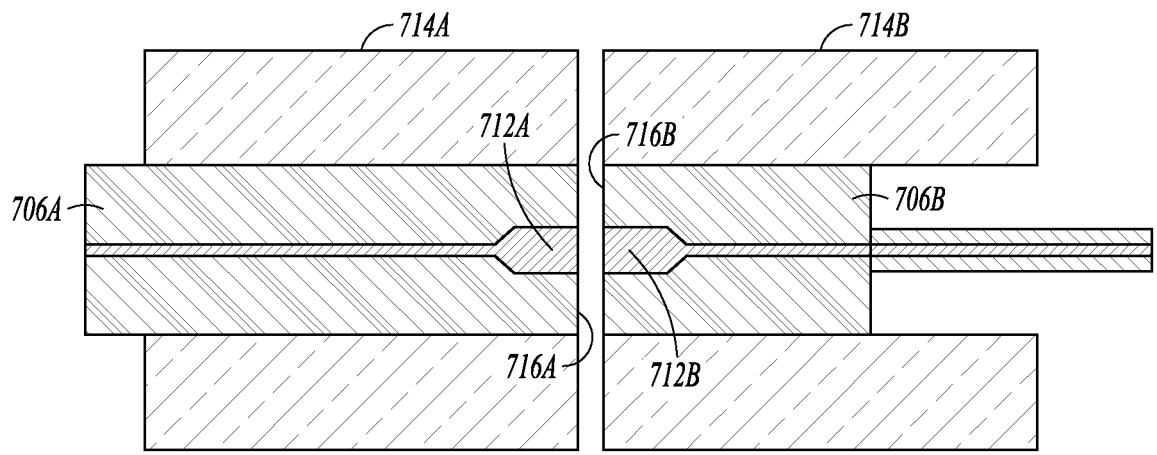
FIG. 15 is a cross-sectional view depicting the cleaved portions inserted into respective connector portions.

FIG. 15 is a cross-sectional view depicting the cleaved portions inserted into respective connector portions. As seen in FIG. 15, the first portion 706A of the cleaved fiber is inserted into a bore, e.g., having a substantially circular cross-section, of a first portion 714A of a connector and the second portion 706B of the cleaved fiber is inserted into a bore, e.g., having a substantially circular cross-section, of a second portion 714B of the connector. In some example configurations, the connector can include a ferrule, e.g., a ceramic ferrule. In some optional implementations, one or both faces 716A, 716B of the optical fiber can be polished, e.g., to optimize performance. In another optional implementation, an anti-reflective (AR) coating can be applied, e.g., to optimize performance.

It should be noted that in some alternative implementations, rather than cleaving the optical fiber into two portions, the cores at the ends of two separate optical fibers can be thermal expanded to a similar size using heating equipment, and then the end faces of these fibers can be prepared to make an optical connection.

FIGS. 11-15 depict an example method of manufacturing a proximal connector in a sensing and/or imaging guidewire. In other examples, however, the techniques shown in FIGS. 11-15 can be rearranged and/or performed in a different order. As an example, the thermal expansion techniques shown in FIG. 13 and be performed before fusion splicing techniques of FIG. 12.

Figure 16:
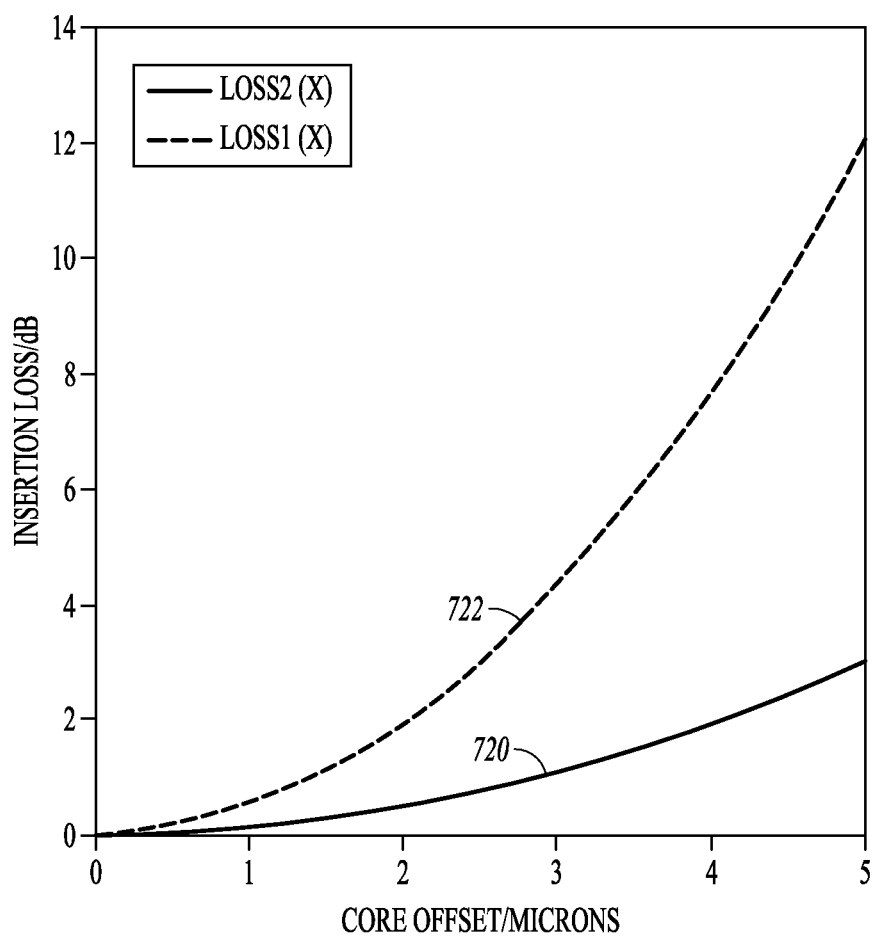
FIG. 16 is a graph depicting insertion loss with respect to mode field diameters and mechanical offset of fiber cores.

FIG. 16 is a graph depicting insertion loss with respect to mode field diameters and mechanical offset of fiber cores. In FIG. 16, the x-axis represents the core offset in microns, and the y-axis represents the insertion loss in decibels (dB). The first trace 720 represents a fiber core with a mode field diameter of 12 µm and the second trace 722 represents a fiber core with a mode field diameter of 6 µm. As seen in FIG. 16, as the core offset increases, the insertion loss of the fiber core with a mode field diameter of 12 µm is significantly lower than the insertion loss of the fiber core with a mode field diameter of 6 µm as the core offset increases.

FIGS. 17A-17B depict an example of a core wire, shown generally at 800, that can be used in combination with an optical fiber pressure sensor. During manufacture, the diameter of the core wire 800 can be varied over specified lengths in order to form a desired shape. For example, as seen in FIG. 17A, the core wire 800 can be manufactured to include a portion 802 with a diameter that is larger than the remaining proximal or distal portions 804, 806, respectively, of the core wire 800. The core wire 800 can be manufactured to include one or more tapered portions 808A-808C that taper the portion 802 from its larger diameter to the smaller diameter of the proximal and distal portions 804, 806.

Figure 18A:
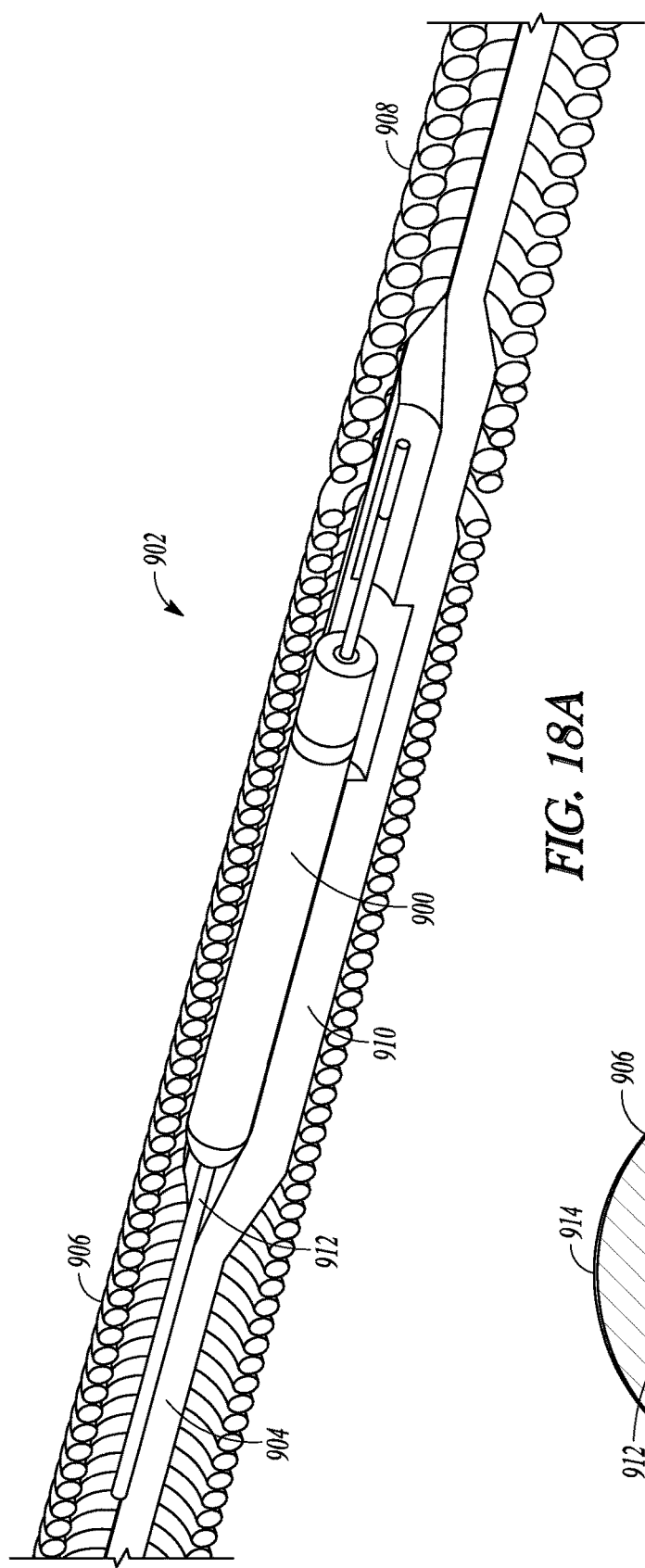
FIG. 18A depicts an example of a guidewire in combination with an optical fiber pressure sensor and the core wire of FIG. 17B.
Figure 18B:
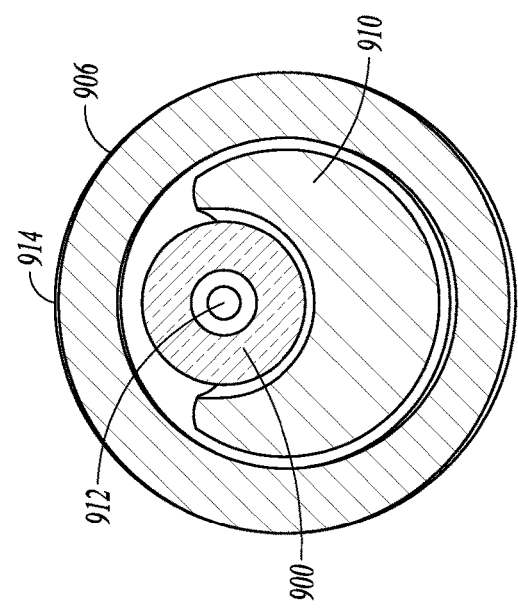
FIG. 18B depicts a cross-sectional view of the configuration shown in FIG. 18A.

After the core wire 800 has been manufactured to the desired dimensions, a cradle can be formed, for example, in enlarged portion 802, e.g., using a coining process, precision machining, micromachining micro EDM, or other processes, in the portion(s) with a larger diameter, as shown generally at 810 in FIG. 17B. The cradle 810 formed in the core wire 800 can be used to provide a housing for a pressure sensor assembly, as shown in FIG. 18A-18B.

The cradle 810 can have varying inside dimensions to provide the ability to secure the sensor in varying ways. For example, in some embodiments, it may be advantageous to mount the sensor at its proximal portion only and to allow the rest of the sensor to be cantilevered in the cavity such that it cannot be touched during normal use of the guidewire. This arrangement can minimize the likelihood of guidewire bending producing erroneous or artificial pressure readings. In other embodiments, the cradle 810 can have a shape that is rectangular or non-rectangular.

By way of example, the cradle 810 as shown can have a shape that enables the mounting of a cylindrical shaped sensor without removing more material than necessary, which helps maintain the relative stiffness of the core in the region of the sensor. The cradle 810, for example, may have a complex shape or it may have a semi-cylindrical shape. By way of example, the cradle of FIG. 17B has a size and shape that by itself does not protect the sensor. The sensor placed therein, as shown in FIG. 18A, can be mounted such that the upper extremity of the cylindrical surface is higher than the side walls of the cradle 810.

Such a cradle and core design can be advantageous because a single structure can function both as the core wire 800 and as the housing of a pressure sensor assembly, which can improve its strength. In addition, the design of FIG. 17B can be advantageous because the core wire 800 is coaxial with the guidewire, as shown in FIG. 18A, which can enhance the performance of the guidewire. For example, the guidewire can improve the steering of the guidewire and allow the guidewire to perform more predictably, e.g., without whip or latency, which can be important while assessing a lesion.

FIG. 18A depicts an example of a guidewire in combination with an optical fiber pressure sensor and the core wire of FIG. 17B. In FIG. 18A, an optical pressure sensor assembly 900 can be delivered to a desired site using a guidewire, shown generally at 902. The guidewire 902 can include a core wire 904, e.g., the core wire 800 of FIG. 8B, a proximal coil 906, and a distal coil 908. As described above, the core wire 904 can be formed to include a cradle 910, e.g., the cradle 810 of FIG. 17B, which can hold the pressure sensor assembly 900. An optical fiber 912 can extend along the core wire 904. As seen in FIG. 18A, the core wire 904 is coaxial with the guidewire 902, which can enhance the performance of the guidewire.

Optical pressure sensor assembly 900 can be seen mounted on the cradle 910 in a cantilevered way. The degree of cantilever can be varied by varying the length of the mount which attaches to the proximal body of 900. The rest of the cavity can be formed such that there is a gap around the distal body and the sensitive distal end of 900. The core wire 904, in the section defining the sensor mount, can be varied in size and shape. For example, the outside diameter of the cradle 910 can have a constant diameter section and one or more tapered sections. The coil 906 can, for example, be attached to the cradle 910 at the constant diameter section and not at the tapered section such that the effect is to minimize the relatively stiff length of the construction in this area. This can be helpful in providing enhancements to the mechanical performance of the guidewire.

In another example, as mentioned in regard to FIG. 17B, the cradle can be sized and shaped such that sensor 900 is not fully protected by the cradle. Such a configuration is shown in the cross-sectional view of FIG. 18B. In this example, coil 906 can form an integral part of the protection means for the sensor 900. The cradle 910, in combination with the coil 906, can form a housing 914 that surrounds the sensor 900 and completes the protection mechanism. The coil 906 and the cradled enlarged portion of the core wire can be joined together to form a solid protection means. The joining process could be a suitable adhesive, solder or braze.

The smaller distal coil diameter (which can result from the larger diameter distal coil wire), shown in the example of a guidewire in combination with an optical fiber pressure sensor of FIG. 18A-18B can be accommodated by reducing the diameter of the ground feature at its distal end. Alternatively, the distal coil inside diameter can be increased by forming the distal coil with a smaller diameter wire or a flattened wire thereby allowing both the proximal and distal coils to fit over the sensor protecting feature on the wire. It may also be advantageous to both reduce the distal diameter of the wire ground feature only slightly and increase the distal coil ID only slightly to fit the distal coil over the sensor protective feature.

VARIOUS NOTES AND EXAMPLES

Example 1 can include or use subject matter (e.g., a system, apparatus, article, or the like) that can include or use an optical connector comprising: a first optical fiber having a first diameter and having a core that includes a thermally expanded core portion adjacent a first end of the first optical fiber;

a second optical fiber spliced to a second end of the first optical fiber, the second optical fiber having a second diameter less than the first diameter; and a connector bore having a first bore portion configured to receive the first end of the first optical fiber.

In Example 2, the optical connector of Example 1 can optionally include, wherein the connector bore includes a second bore portion, the connector further comprising: a third optical fiber having the first diameter and having a core that includes a thermally expanded core portion adjacent a first end of the third optical fiber; wherein the second bore portion is configured to receive the first end of the third optical fiber, and wherein the first bore portion and the second bore portion are configured to at least partially align the thermally expanded core portion of the first optical fiber with the thermally expanded core portion of the third optical fiber.

In Example 3, the optical connector of any of Examples 1 and 2 can optionally include, wherein the connector bore comprises a ceramic ferrule.

In Example 4, the optical connector of any of claims 1-3 can optionally include, wherein at least one of the first end of the first optical fiber and the first end of the third optical fiber is polished.

In Example 5, the optical connector of any of Examples 1-4 can optionally include, wherein at least one of the first end of the first optical fiber and the first end of the third optical fiber includes an anti-reflection coating.

In Example 6, the optical connector of any of Examples 1-5 can optionally include, an adhesive to adhere at least a portion of the first optical fiber to the first bore.

Example 7 can include or use subject matter (e.g., a method or the like) that can include or use a method of manufacturing a connector, the method comprising: fusion splicing an end of a first optical fiber having a first diameter to an end of a second optical fiber having a second diameter less than the first diameter; thermally expanding a portion of a core of the first optical fiber; inserting the first optical fiber into a bore of a first portion of the connector and inserting a third optical fiber into a bore of a second portion of the connector, wherein the third optical fiber includes an expanded core portion configured to at least partially align with the thermally expanded portion of the core of the first optical fiber.

In Example 8, the method of Example 7 can optionally include, prior to the inserting, cleaving the first optical fiber through the thermally expanded portion into a first optical fiber portion and a second optical fiber portion, wherein the first optical fiber includes the first optical fiber portion, and wherein the third optical fiber includes the second optical fiber portion.

In Example 9, the method of Example 7 can optionally include, prior to the inserting, thermally expanding a portion of a core of the third optical fiber.

In Example 10, the method of any of Examples 7-9 can optionally include, polishing at least one of an end of the first optical fiber portion and an end of the second optical fiber portion.

In Example 11, the method of any of Examples 7-10 can optionally include, applying an anti-reflection coating to at least one of an end of the first optical fiber portion and an end of the second optical fiber portion.

In Example 12, the method of any of Examples 7-11 can optionally include, applying an adhesive to adhere at least a portion of the first optical fiber to the first portion of the connector.

In Example 13, the method of any of Examples 7-12 can optionally include, wherein inserting the first optical fiber into a bore of a first portion of the connector and inserting the third optical fiber into a bore of a second portion of the connector comprises: inserting the first optical fiber into a bore of a ceramic ferrule of a first portion of the connector and inserting the third optical fiber into a bore of a ceramic ferrule of a second portion of the connector.

In Example 14, the method of any of Examples 7-13 can optionally include,
wherein fusion splicing an end of a first optical fiber having a first diameter to an end of a second optical fiber having a second diameter less than the first diameter comprises: fusion splicing an end of a first optical fiber having a first diameter of about 125 micrometers to an end of a second optical fiber having a second diameter less than 50 micrometers.

In Example 15, the method of any of Examples 7-14 can optionally include, wherein fusion splicing an end of a first optical fiber having a first diameter to an end of a second optical fiber having a second diameter less than the first diameter comprises: applying heat using a laser.

In Example 16, the method of any of Examples 7-15 can optionally include, wherein fusion splicing an end of a first optical fiber having a first diameter to an end of a second optical fiber having a second diameter less than the first diameter is performed after the thermally expanding a portion of a core of the first optical fiber.

In Example 17, the method of any of Examples 7-15 can optionally include, wherein fusion splicing an end of a first optical fiber having a first diameter to an end of a second optical fiber having a second diameter less than the first diameter is performed before the thermally expanding a portion of a core of the first optical fiber.

Example 18 can include or use subject matter (e.g., a method or the like) that can include or use a method of manufacturing a connector, the method comprising: fusion splicing an end of a first optical fiber having a first diameter to an end of a second optical fiber having a second diameter less than the first diameter; thermally expanding a portion of a core of the first optical fiber; cleaving the first optical fiber through the thermally expanded portion into a first optical fiber portion and a second optical fiber portion; inserting the first optical fiber portion into a bore of a ceramic ferrule of a first portion of the connector and inserting the second optical fiber portion into a bore of a ceramic ferrule of a second portion of the connector; polishing at least one of an end of the first optical fiber portion and an end of the second optical fiber portion; and applying an anti-reflection coating to at least one of an end of the first optical fiber portion and an end of the second optical fiber portion.

Example 19 can include or use subject matter (e.g., a system, apparatus, article, or the like) that can include or use an apparatus comprising: an elongated assembly, at least a portion of which is sized, shaped, or otherwise configured to be inserted into a human body to measure a physiological parameter at an internal location within the body, wherein the elongated assembly includes: a guidewire having a length; and a multimode optical fiber, extending longitudinally along the guidewire, the optical fiber configured to communicate light between a location outside of the body and a portion of the optical fiber that is to be located at or near the internal location within the body at which the physiological parameter is to be measured, the optical fiber having a diameter of less than 50 micrometers.

In Example 20, the apparatus of Example 19 can optionally include, wherein the physiological parameter is a pressure, and wherein the apparatus comprises an optical fiber pressure sensor configured to be located on the elongated assembly to allow positioning at or near the internal location within the body at which pressure is to be measured.

In Example 21, the apparatus of any of Examples 19 and 20 can optionally include, wherein the optical fiber pressure sensor comprises a diaphragm configured to respond to a change in the pressure.

In Example 22, the apparatus of any of Examples 19-21 can optionally include, wherein the optical fiber has a diameter of about 25 micrometers, wherein the optical fiber includes a core, and wherein the core has a diameter of about 23 micrometers.

In Example 23, the apparatus of any of Examples 19-22 can optionally include, wherein the core of the optical fiber comprises borosilicate glass.

In Example 24, the apparatus of any of Examples 19-23 can optionally include, wherein the optical fiber comprises a dopant material to change a refractive index of the optical fiber.

In Example 25, the apparatus of Example 24 can optionally include, wherein the dopant material is added to an outer diameter layer of the optical fiber.

In Example 26, the apparatus of any of Examples 19-25 can optionally include, wherein the optical fiber further comprises a cladding including silica glass, the cladding disposed about the core and configured with a refractive index creating a light guide in the optical fiber.

Example 27 can include or use subject matter (e.g., a system, apparatus, article, or the like) that can include or use an apparatus comprising: an elongated assembly, at least a portion of which is sized, shaped, or otherwise configured to be inserted into a human body to measure a physiological parameter at an internal location within the body, wherein the elongated assembly includes: a guidewire having a length; and a multimode optical fiber extending longitudinally along the guidewire, the optical fiber configured to communicate light between a location outside of the body and a portion of the optical fiber that is to be located at or near the internal location within the body at which the physiological parameter is to be measured, the optical fiber having a diameter of less than 50 micrometers; a pressure sensor assembly attached to a distal end region of the optical fiber, the pressure sensor assembly including: at least one tubular member having an inner diameter and configured to be bonded to and extend beyond a distal end of the optical fiber; a diaphragm bonded to a distal end of the tubular member and configured to respond to a change in pressure, wherein the diaphragm, the optical fiber and the inner diameter of the tubular member define a cavity adjacent the distal end of the optical fiber.

In Example 28, the apparatus of Example 27 can optionally include, wherein the diaphragm includes silicon.

In Example 29, the apparatus of Example 27 can optionally include, wherein the diaphragm includes glass.

In Example 30, the apparatus of any of Examples 27-29 can optionally include, wherein the diaphragm has a thickness of about 5 micrometers or less.

Example 31 can include or use subject matter (e.g., a system, apparatus, article, or the like) that can include or use an apparatus comprising: an elongated assembly, at least a portion of which is sized, shaped, or otherwise configured to be inserted into a human body to measure a physiological parameter at an internal location within the body, wherein the elongated assembly includes: a guidewire having a length; a pressure sensor housing coupled to the guidewire; an optical fiber extending longitudinally along the guidewire, the optical fiber configured to communicate light between a location outside of the body and a portion of the optical fiber that is to be located at or near the internal location within the body at which the physiological parameter is to be measured; a collar configured to be bonded to the pressure sensor housing and the optical fiber; and a pressure sensor assembly bonded to a distal end region of the optical fiber, the pressure sensor assembly positioned distal to and spaced apart from the collar, the pressure sensor assembly positioned within and spaced apart from the pressure sensor housing.

In Example 32, the apparatus of Example 31 can optionally include, wherein the collar comprises fused silica.

In Example 33, the apparatus of Example 31 can optionally include, wherein the collar comprises borosilicate glass.

In Example 34, the apparatus of any of Examples 31-33 can optionally include, wherein the collar is cylindrical.

In Example 35, the apparatus of any of Examples 31-34 can optionally include, wherein the collar is a cylindrical tube.

In Example 36, the apparatus of any of Examples 31-35 can optionally include, wherein the collar configured to be bonded to the pressure sensor housing and the optical fiber is bonded using solder glass bonding techniques.

In Example 37, the apparatus of any of Examples 31-36 can optionally include, wherein the collar configured to be bonded to the pressure sensor housing and the optical fiber is bonded using fusion splicing.

Example 38 can include or use subject matter (e.g., a system, apparatus, article, or the like) that can include or use an apparatus comprising: an optical fiber; and an optical fiber sensor including at least one Fiber Bragg Grating (FBG), wherein the sensor is coupled to the optical fiber using solder glass.

In Example 39, the apparatus of Example 38 can optionally include, wherein the sensor and at least a portion of the optical fiber is configured to be inserted into a human body to measure a physiological parameter at an internal location within the body.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus comprising:
an elongated assembly, at least a portion of which is sized, shaped, or otherwise configured to be inserted into a human body to measure a physiological parameter at an internal location within the body, wherein the elongated assembly includes:
a guidewire having a length and having guidewire coils;
an optical fiber extending longitudinally along the guidewire, the optical fiber configured to communicate light between a location outside of the body and a portion of the optical fiber that is to be located at or near the internal location within the body at which the physiological parameter is to be measured;

a pressure sensor coupled to the optical fiber;

a core wire including a cradle integrally formed with the core wire, wherein the cradle is sized and arranged to support the pressure sensor and being covered by the guidewire coils, and wherein the core wire is coupled to the guidewire;

a pressure sensor housing, wherein the cradle defines a portion of the pressure sensor housing, and wherein the pressure sensor is cantilevered within the cradle; and a collar bonded to the pressure sensor housing and to the optical fiber such that the pressure sensor is physically isolated from the pressure sensor housing and the guidewire, wherein the pressure sensor is bonded to a distal end region of the optical fiber, wherein the pressure sensor is positioned distal to and spaced apart from the collar, and wherein the pressure sensor is positioned within and spaced apart from the pressure sensor housing.

2. The apparatus of claim 1, wherein the collar comprises at least one of fused silica and borosilicate glass.

3. The apparatus of claim 1, wherein the collar is a cylindrical tube.

4. The apparatus of claim 1, wherein the optical fiber is bonded using at least one of solder glass bonding techniques and fusion splicing.

5. The apparatus of claim 1, wherein the pressure sensor housing includes:

a proximal housing portion and a distal housing portion separated by a window portion.

6. The apparatus of claim 5, wherein the window portion includes a gasket.

7. The apparatus of claim 6, wherein the gasket is made of at least one material capable of deforming or bending without fracture or cracking.

8. The apparatus of claim 1, wherein the pressure sensor includes a sensing region having first and second fiber Bragg gratings located in an optical fiber core of the optical fiber.

9. The apparatus of claim 8, wherein one of the first and second fiber Bragg gratings located in the optical fiber core of the optical fiber extends distally beyond a distal end of a housing of the pressure sensor.

10. The apparatus of claim 8, wherein each of the first and second fiber Bragg gratings includes a phase shift.

11. The apparatus of claim 8, comprising:

a non-reflective termination adjacent to a distal end of the second fiber Bragg grating.

12. The apparatus of claim 1, wherein the pressure sensor is temperature compensated.

13. The apparatus of claim 12, wherein the temperature compensated pressure sensor includes a sensing region having first and second fiber Bragg gratings (FBG).

14. The apparatus of claim 13, wherein the first FBG is configured to measure both pressure and temperature and the second FBG is configured to measure temperature.

15. An apparatus comprising:

an elongated assembly, at least a portion of which is sized, shaped, or otherwise configured to be inserted into a human body to measure a physiological parameter at an internal location within the body, wherein the elongated assembly includes:

a guidewire having a length and having guidewire coils;

an optical fiber extending longitudinally along the guidewire, the optical fiber configured to communicate light between a location outside of the body and a portion of the optical fiber that is to be located at or near the internal location within the body at which the physiological parameter is to be measured;

a pressure sensor coupled to the optical fiber;

a solid core wire extending through guidewire coils of the guidewire, the solid core wire including a cradle integrally formed with the core wire, wherein the cradle is sized and arranged to support the pressure sensor and being covered by the guidewire coils, and wherein the solid core wire is coupled to the guidewire;

a pressure sensor housing, wherein the cradle defines a portion of the pressure sensor housing, wherein the cradle only partially encloses the pressure sensor, and wherein the pressure sensor is cantilevered within the cradle; and a collar bonded to the pressure sensor housing and to the optical fiber such that the pressure sensor is physically isolated from the pressure sensor housing and the guidewire, wherein the pressure sensor is bonded to a distal end region of the optical fiber, wherein the pressure sensor is positioned distal to and spaced apart from the collar, and wherein the pressure sensor is positioned within and spaced apart from the pressure sensor housing.

16. The apparatus of claim 15, wherein the collar comprises at least one of fused silica and borosilicate glass.

17. The apparatus of claim 15, wherein the collar is a cylindrical tube.

18. The apparatus of claim 15, wherein the optical fiber is bonded using at least one of solder glass bonding techniques and fusion splicing.

* * * * *